(12) United States Patent
Lin et al.

(10) Patent No.: US 8,609,831 B2
(45) Date of Patent: Dec. 17, 2013

(54) RNA-MEDIATED GENE MODULATION

(75) Inventors: Shi-Lung Lin, Alhambra, CA (US);
Shao-Yao Ying, San Marino, CA (US)

(73) Assignee: University of Southern California, Los Angeles, CA (US)

( * ) Notice: Subject to any disclaimer, the term of this patent is extended or adjusted under 35 U.S.C. 154(b) by 1456 days.

(21) Appl. No.: 10/663,875

(22) Filed: Sep. 16, 2003

(65) Prior Publication Data
US 2004/0253604 A1  Dec. 16, 2004

Related U.S. Application Data

(60) Provisional application No. 60/411,062, filed on Sep. 16, 2002, provisional application No. 60/418,405, filed on Oct. 12, 2002.

(51) Int. Cl.
*C07H 21/04* (2006.01)

(52) U.S. Cl.
USPC .................. 536/24.5; 536/24.31; 536/24.1

(58) Field of Classification Search
None
See application file for complete search history.

(56) References Cited

U.S. PATENT DOCUMENTS

| | | | |
|---|---|---|---|
| 6,013,487 A * | 1/2000 | Mitchell | 435/91.3 |
| 6,506,559 B1 | 1/2003 | Fire et al. | |
| 6,710,174 B2 * | 3/2004 | Bennett et al. | 536/24.5 |
| 7,393,632 B2 * | 7/2008 | Cheo et al. | 435/6 |

OTHER PUBLICATIONS

Zhuang et al. UACUAAC is the preferred branch site for mammalian mRNA splicing. PNAS 1989: 2752-2756.*
Krawxzak et al. The mutational spectrum of single base-pair substitutions in mRNA splice junctions of human genes: causes and consequences. Human Genet 1992, vol. 90: 41-54.*
Coolidge et al. Functional analysis of the polypyrimidine tract in pre-mRNA splicing. Nucleic Acids Research 1997, vol. 25, No. 4: 888-896.*
Davey et al. Reduced expression of alpha5beta1 integrin prevents spreading-dependent cell proliferation. Journal of Cell Science 112; 4663-4672, 1999.*
Holen et al. (2002) Nucleic Acids Res. 30:1757-1766Holen et al. (2002) Nucleic Acids Res. 30:1757-1766.*
Abrams et al. (J. Biol. Chem 264(24):14016-14021, 1989).*
Lau et al. (Science 294:858-862, 2001).*
Lin et al., "D-RNAi (messenger RNA-antisense DNA interference) as a novel defense system against cancer and viral infections", Current Cancer Drug Targets, 2001, vol. 1, pp. 214-247.
Lin et al., "A novel mRNA-cDNA interference phenomenon for silencing bcl-2 expression in human LNCaP cells", Biochemical and Biophysical Research Communications, 2001, vol. 281, pp. 639-644.

* cited by examiner

*Primary Examiner* — Kimberly Chong
(74) *Attorney, Agent, or Firm* — DLA Piper LLP (US)

(57) ABSTRACT

An isolated RNA comprising an intron RNA that is released in a cell, thereby modulating the function of a target gene. Also disclosed are a composition comprising a chemokine and an isolated RNA of the invention or a DNA template for the isolated RNA, a composition comprising one or more agents that induce RNA-mediated modulation of the functions of two or more target genes in a cell, and methods of using these compositions for modulating the functions of genes in a cell.

12 Claims, 11 Drawing Sheets

SpRNAi-antisense RNA production:

FIG.3 SpRNAi-sense RNA or -dsRNA production:

FIG.4 SpRNAi-shRNA production:

FIG.10
(A)
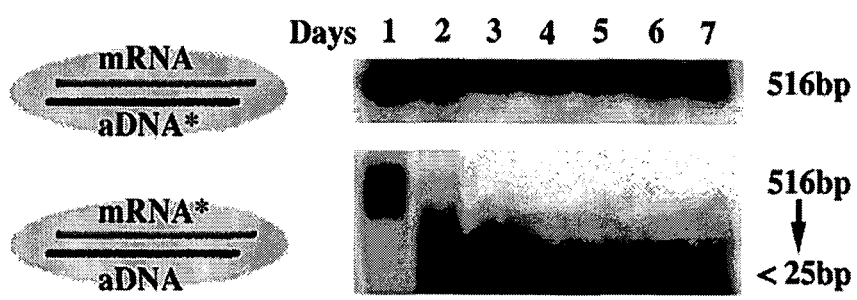
(B)
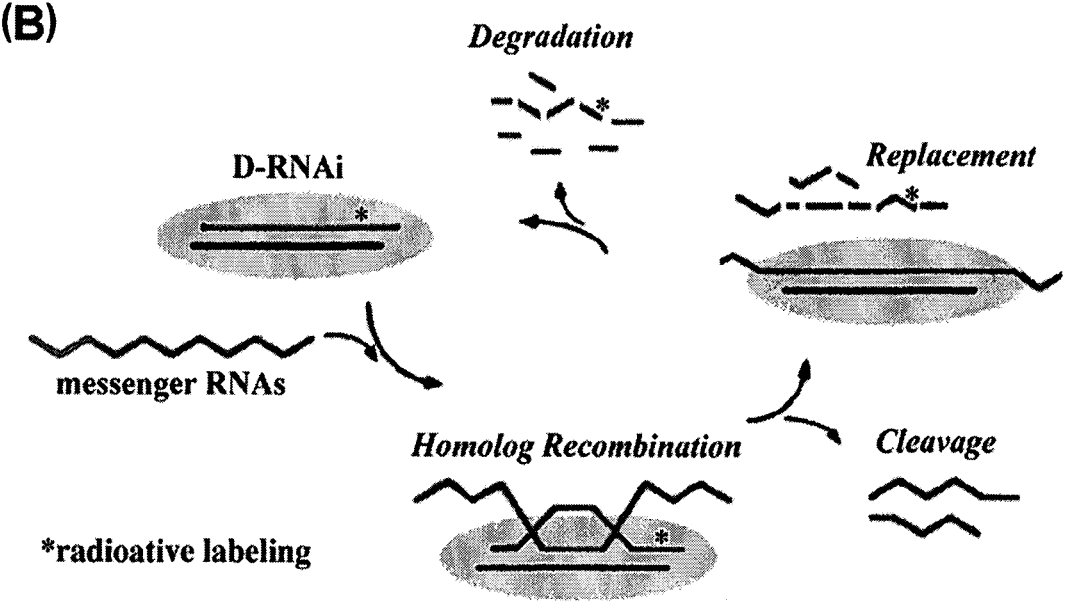

SEQUENCE LISTING

```
<160> NUMBER OF SEQ ID NOS: 32

<210> SEQ ID NO 1
<211> LENGTH: 10
<212> TYPE: RNA
<213> ORGANISM: Artificial
<220> FEATURE:
```

-continued

```
<223> OTHER INFORMATION: Splice acceptor
<220> FEATURE:
<221> NAME/KEY: misc_feature
<222> LOCATION: (2)..(2)
<223> OTHER INFORMATION: n represents a, u or none
<220> FEATURE:
<221> NAME/KEY: misc_feature
<222> LOCATION: (3)..(3)
<223> OTHER INFORMATION: k represents u or g
<220> FEATURE:
<221> NAME/KEY: misc_feature
<222> LOCATION: (4)..(4)
<223> OTHER INFORMATION: s represents c or g
<220> FEATURE:
<221> NAME/KEY: misc_feature
<222> LOCATION: (6)..(6)
<223> OTHER INFORMATION: y represents u or c
<220> FEATURE:
<221> NAME/KEY: misc_feature
<222> LOCATION: (7)..(7)
<223> OTHER INFORMATION: r represents g or a

<400> SEQUENCE: 1 gnkscyrcag                                                              10

<210> SEQ ID NO 2
<211> LENGTH: 21
<212> TYPE: RNA
<213> ORGANISM: Artificial
<220> FEATURE:
<223> OTHER INFORMATION: Poly-pyrimidine tract
<220> FEATURE:
<221> NAME/KEY: misc_feature
<222> LOCATION: (2)..(2)
<223> OTHER INFORMATION: y represents c or u
<220> FEATURE:
<221> NAME/KEY: misc_feature
<222> LOCATION: (3)..(4)
<223> OTHER INFORMATION: nn represents uy or none-none, y represents c
      or u
<220> FEATURE:
<221> NAME/KEY: misc_feature
<222> LOCATION: (5)..(6)
<223> OTHER INFORMATION: nn represents uy or none-none, y represents c
      or u
<220> FEATURE:
<221> NAME/KEY: misc_feature
<222> LOCATION: (7)..(7)
<223> OTHER INFORMATION: n represents c or none
<220> FEATURE:
<221> NAME/KEY: misc_feature
<222> LOCATION: (15)..(19)
<223> OTHER INFORMATION: n represents u or none
<220> FEATURE:
<221> NAME/KEY: misc_feature
<222> LOCATION: (21)..(21)
<223> OTHER INFORMATION: n represents c or none

<400> SEQUENCE: 2
uynnnnnuuu uuuunnnnnc n                                                 21

<210> SEQ ID NO 3
<211> LENGTH: 30
<212> TYPE: RNA
<213> ORGANISM: Artificial
<220> FEATURE:
<223> OTHER INFORMATION: Poly-pyrimidine tract
<220> FEATURE:
<221> NAME/KEY: misc_feature
<222> LOCATION: (15)..(16)
<223> OTHER INFORMATION: nn represents uc or none-none
<220> FEATURE:
<221> NAME/KEY: misc_feature
<222> LOCATION: (17)..(18)
<223> OTHER INFORMATION: nn represents uc or none-none
<220> FEATURE:
```

```
<221> NAME/KEY: misc_feature
<222> LOCATION: (19)..(20)
<223> OTHER INFORMATION: nn represents uc or none-none
<220> FEATURE:
<221> NAME/KEY: misc_feature
<222> LOCATION: (21)..(22)
<223> OTHER INFORMATION: nn represents uc or none-none
<220> FEATURE:
<221> NAME/KEY: misc_feature
<222> LOCATION: (23)..(24)
<223> OTHER INFORMATION: nn represents uc or none-none
<220> FEATURE:
<221> NAME/KEY: misc_feature
<222> LOCATION: (25)..(25)
<223> OTHER INFORMATION: n represents a, g, c or u
<220> FEATURE:
<221> NAME/KEY: misc_feature
<222> LOCATION: (30)..(30)
<223> OTHER INFORMATION: n represents g or none

<400> SEQUENCE: 3
ucucucucuc ucucnnnnnn nnnnncuagn                                    30

<210> SEQ ID NO 4
<211> LENGTH: 12
<212> TYPE: RNA
<213> ORGANISM: Artificial
<220> FEATURE:
<223> OTHER INFORMATION: Splice donor

<400> SEQUENCE: 4
agguaagagg au                                                       12

<210> SEQ ID NO 5
<211> LENGTH: 10
<212> TYPE: RNA
<213> ORGANISM: Artificial
<220> FEATURE:
<223> OTHER INFORMATION: Splice donor

<400> SEQUENCE: 5
agguaagagu                                                          10

<210> SEQ ID NO 6
<211> LENGTH: 13
<212> TYPE: RNA
<213> ORGANISM: Artificial
<220> FEATURE:
<223> OTHER INFORMATION: Splice acceptor

<400> SEQUENCE: 6
gauauccugc agg                                                      13

<210> SEQ ID NO 7
<211> LENGTH: 42
<212> TYPE: DNA
<213> ORGANISM: Artificial
<220> FEATURE:
<223> OTHER INFORMATION: Oligonucleotide

<400> SEQUENCE: 7
gtaagaggat ccgatcgcag gagcgcacca tcttcttcaa ga                      42

<210> SEQ ID NO 8
<211> LENGTH: 46
<212> TYPE: DNA
<213> ORGANISM: Artificial
<220> FEATURE:
<223> OTHER INFORMATION: Oligonucleotide
```

```
<400> SEQUENCE: 8
cgcgtcttga agaagatggt gcgctcctgc gatcggatcc tcttac        46

<210> SEQ ID NO 9
<211> LENGTH: 42
<212> TYPE: DNA
<213> ORGANISM: Artificial
<220> FEATURE:
<223> OTHER INFORMATION: Oligonucleotide

<400> SEQUENCE: 9
gtaagaggat ccgatcgctt gaagaagatg gtgcgctcct ga            42

<210> SEQ ID NO 10
<211> LENGTH: 46
<212> TYPE: DNA
<213> ORGANISM: Artificial
<220> FEATURE:
<223> OTHER INFORMATION: Oligonucleotide

<400> SEQUENCE: 10
cgcgtcagga gcgcaccatc ttcttcaagc gatcggatcc tcttac        46

<210> SEQ ID NO 11
<211> LENGTH: 70
<212> TYPE: DNA
<213> ORGANISM: Artificial
<220> FEATURE:
<223> OTHER INFORMATION: Oligonucleotide

<400> SEQUENCE: 11
gtaagaggat ccgatcgcag gagcgcacca tcttcttcaa gttaacttga agaagatggt    60
gcgctcctga                                                           70

<210> SEQ ID NO 12
<211> LENGTH: 74
<212> TYPE: DNA
<213> ORGANISM: Artificial
<220> FEATURE:
<223> OTHER INFORMATION: Oligonucleotide

<400> SEQUENCE: 12
cgcgtcagga gcgcaccatc ttcttcaagt taacttgaag aagatggtgc gctcctgcga    60
tcggatcctc ttac                                                      74

<210> SEQ ID NO 13
<211> LENGTH: 47
<212> TYPE: DNA
<213> ORGANISM: Artificial
<220> FEATURE:
<223> OTHER INFORMATION: Oligonucleotide

<400> SEQUENCE: 13
cgcgttacta actggtacct cttctttttt ttttgatat cctgcag        47

<210> SEQ ID NO 14
<211> LENGTH: 45
<212> TYPE: DNA
<213> ORGANISM: Artificial
<220> FEATURE:
<223> OTHER INFORMATION: Oligonucleotide

<400> SEQUENCE: 14
gtcctgcagg atatcaaaaa aaaaagaaga ggtaccagtt agtaa          45
```

```
<210> SEQ ID NO 15
<211> LENGTH: 27
<212> TYPE: DNA
<213> ORGANISM: Artificial
<220> FEATURE:
<223> OTHER INFORMATION: Primer

<400> SEQUENCE: 15
ctcgagcatg gtgagcggcc tgctgaa                                27

<210> SEQ ID NO 16
<211> LENGTH: 27
<212> TYPE: DNA
<213> ORGANISM: Artificial
<220> FEATURE:
<223> OTHER INFORMATION: Primer

<400> SEQUENCE: 16
tctagaagtt ggccttctcg ggcaggt                                27

<210> SEQ ID NO 17
<211> LENGTH: 25
<212> TYPE: DNA
<213> ORGANISM: Artificial
<220> FEATURE:
<223> OTHER INFORMATION: Oligonucleotide

<400> SEQUENCE: 17
cgcaagcagg gccaaattgt gggta                                  25

<210> SEQ ID NO 18
<211> LENGTH: 31
<212> TYPE: DNA
<213> ORGANISM: Artificial
<220> FEATURE:
<223> OTHER INFORMATION: Oligonucleotide

<400> SEQUENCE: 18
tagcacccac aatttggccc tgcttgtgcg c                           31

<210> SEQ ID NO 19
<211> LENGTH: 25
<212> TYPE: DNA
<213> ORGANISM: Artificial
<220> FEATURE:
<223> OTHER INFORMATION: Oligonucleotide

<400> SEQUENCE: 19
cgacccacaa tttggccctg cttga                                  25

<210> SEQ ID NO 20
<211> LENGTH: 31
<212> TYPE: DNA
<213> ORGANISM: Artificial
<220> FEATURE:
<223> OTHER INFORMATION: Oligonucleotide

<400> SEQUENCE: 20
tagccaagca gggccaaatt gtgggttgcg c                           31

<210> SEQ ID NO 21
<211> LENGTH: 51
<212> TYPE: DNA
<213> ORGANISM: Artificial
<220> FEATURE:
<223> OTHER INFORMATION: Oligonucleotide
```

-continued

```
<400> SEQUENCE: 21
cgcaagcagg gccaaattgt gggtttaaac ccacaatttg gccctgcttg a        51

<210> SEQ ID NO 22
<211> LENGTH: 57
<212> TYPE: DNA
<213> ORGANISM: Artificial
<220> FEATURE:
<223> OTHER INFORMATION: Oligonucleotide

<400> SEQUENCE: 22
tagcacccac aatttggccc tgcttgaatt caagcagggc caaattgtgg gttgcgc   57

<210> SEQ ID NO 23
<211> LENGTH: 75
<212> TYPE: DNA
<213> ORGANISM: Artificial
<220> FEATURE:
<223> OTHER INFORMATION: Probe

<400> SEQUENCE: 23
cctggccccc tgctgcgagt acggcagcag gacgtaagag gatccgatcg caggagcgca  60
ccatcttctt caagt                                                   75

<210> SEQ ID NO 24
<211> LENGTH: 10
<212> TYPE: DNA
<213> ORGANISM: Artificial
<220> FEATURE:
<223> OTHER INFORMATION: Splice donor
<220> FEATURE:
<221> NAME/KEY: misc_feature
<222> LOCATION: (6)..(6)
<223> OTHER INFORMATION: n represents a or none
<220> FEATURE:
<221> NAME/KEY: misc_feature
<222> LOCATION: (10)..(10)
<223> OTHER INFORMATION: k represents g or t

<400> SEQUENCE: 24 aggtangagk                                                        10

<210> SEQ ID NO 25
<211> LENGTH: 12
<212> TYPE: DNA
<213> ORGANISM: Artificial
<220> FEATURE:
<223> OTHER INFORMATION: Splice donor

<400> SEQUENCE: 25
aggtaagagg at                                                     12

<210> SEQ ID NO 26
<211> LENGTH: 10
<212> TYPE: DNA
<213> ORGANISM: Artificial
<220> FEATURE:
<223> OTHER INFORMATION: Splice donor

<400> SEQUENCE: 26
aggtaagagt                                                        10

<210> SEQ ID NO 27
<211> LENGTH: 11
<212> TYPE: DNA
<213> ORGANISM: Artificial
<220> FEATURE:
```

```
<223> OTHER INFORMATION: Splice acceptor
<220> FEATURE:
<221> NAME/KEY: misc_feature
<222> LOCATION: (2)..(2)
<223> OTHER INFORMATION: n represents w or none, w represents a or t
<220> FEATURE:
<221> NAME/KEY: misc_feature
<222> LOCATION: (3)..(3)
<223> OTHER INFORMATION: k represents t or g
<220> FEATURE:
<221> NAME/KEY: misc_feature
<222> LOCATION: (4)..(4)
<223> OTHER INFORMATION: s represents c or g
<220> FEATURE:
<221> NAME/KEY: misc_feature
<222> LOCATION: (6)..(6)
<223> OTHER INFORMATION: y represents t or c
<220> FEATURE:
<221> NAME/KEY: misc_feature
<222> LOCATION: (7)..(7)
<223> OTHER INFORMATION: r represents g or a
<220> FEATURE:
<221> NAME/KEY: misc_feature
<222> LOCATION: (11)..(11)
<223> OTHER INFORMATION: s represents g or c

<400> SEQUENCE: 27
gnkscyrcag s                                                         11

<210> SEQ ID NO 28
<211> LENGTH: 13
<212> TYPE: DNA
<213> ORGANISM: Artificial
<220> FEATURE:
<223> OTHER INFORMATION: Splice acceptor

<400> SEQUENCE: 28
gatatcctgc agg                                                       13

<210> SEQ ID NO 29
<211> LENGTH: 15
<212> TYPE: DNA
<213> ORGANISM: Artificial
<220> FEATURE:
<223> OTHER INFORMATION: Poly-pyrimidine tract

<400> SEQUENCE: 29
tcttcttttt ttttt                                                     15

<210> SEQ ID NO 30
<211> LENGTH: 14
<212> TYPE: DNA
<213> ORGANISM: Artificial
<220> FEATURE:
<223> OTHER INFORMATION: Splice acceptor

<400> SEQUENCE: 30
gatatcctgc aggc                                                      14

<210> SEQ ID NO 31
<211> LENGTH: 21
<212> TYPE: DNA
<213> ORGANISM: Artificial
<220> FEATURE:
<223> OTHER INFORMATION: Poly-pyrimidine tract
<220> FEATURE:
<221> NAME/KEY: misc_feature
<222> LOCATION: (2)..(2)
<223> OTHER INFORMATION: y represents c or t
<220> FEATURE:
<221> NAME/KEY: misc_feature
<222> LOCATION: (3)..(4)
```

```
<223> OTHER INFORMATION: nn represents ty or none-none, y represents c
      or t
<220> FEATURE:
<221> NAME/KEY: misc_feature
<222> LOCATION: (5)..(6)
<223> OTHER INFORMATION: nn represents ty or none-none, y represents c
      or t
<220> FEATURE:
<221> NAME/KEY: misc_feature
<222> LOCATION: (7)..(7)
<223> OTHER INFORMATION: n represents c or none
<220> FEATURE:
<221> NAME/KEY: misc_feature
<222> LOCATION: (15)..(19)
<223> OTHER INFORMATION: n represents t or none
<220> FEATURE:
<221> NAME/KEY: misc_feature
<222> LOCATION: (21)..(21)
<223> OTHER INFORMATION: n represents c or none

<400> SEQUENCE: 31
tynnnnnttt ttttnnnnnc n                                            21

<210> SEQ ID NO 32
<211> LENGTH: 30
<212> TYPE: DNA
<213> ORGANISM: Artificial
<220> FEATURE:
<223> OTHER INFORMATION: Poly-pyrimidine tract
<220> FEATURE:
<221> NAME/KEY: misc_feature
<222> LOCATION: (15)..(16)
<223> OTHER INFORMATION: nn represents tc or none-none
<220> FEATURE:
<221> NAME/KEY: misc_feature
<222> LOCATION: (17)..(18)
<223> OTHER INFORMATION: nn represents tc or none-none
<220> FEATURE:
<221> NAME/KEY: misc_feature
<222> LOCATION: (19)..(20)
<223> OTHER INFORMATION: nn represents tc or none-none
<220> FEATURE:
<221> NAME/KEY: misc_feature
<222> LOCATION: (21)..(22)
<223> OTHER INFORMATION: nn represents tc or none-none
<220> FEATURE:
<221> NAME/KEY: misc_feature
<222> LOCATION: (23)..(24)
<223> OTHER INFORMATION: nn represents tc or none-none
<220> FEATURE:
<221> NAME/KEY: misc_feature
<222> LOCATION: (25)..(25)
<223> OTHER INFORMATION: n represents a, g, c or t
<220> FEATURE:
<221> NAME/KEY: misc_feature
<222> LOCATION: (30)..(30)
<223> OTHER INFORMATION: n represents g or none

<400> SEQUENCE: 32
tctctctctc tctcnnnnnn nnnnnctagn                                   30
```

RNA-MEDIATED GENE MODULATION

RELATED APPLICATIONS

This application claims priority to U.S. Provisional Application Serial No. 60/411,062, filed Sep. 16, 2002, and U.S. Provisional Application Serial No. 60/418,405, filed Oct. 12, 2002, the contents of which are incorporated herein by reference.

This invention was made with support in part by a grant from NIH (CA 85722). Therefore, the U.S. government has certain rights.

TECHNICAL FIELD

This invention relates to regulation of a gene function.

BACKGROUND

One strategy for treating human diseases is to target specific disease-associated genes by either replacing impaired gene functions or by suppressing unwanted gene functions. Expression vectors are commonly used for introducing active genes into a cell to provide missing gene functions. To suppress unwanted gene functions, antisense oligonucleotides, antibodies, and small molecule drugs are often used as therapeutic agents.

Applications of RNA interference (RNAi) (Elbashir et al. (2001) Nature 411: 494-498) and deoxyribonucleotidylated-RNA interfering (D-RNAi) (Lin et al. (2001) Biochem. Biophys. Res. Commun. 281: 639-644) technologies in treating human diseases are also in progress. RNAi elicits post-transcriptional gene silencing (PTGS) phenomena, knocking down specific gene expression with high potency and less toxicity than traditional antisense gene therapies. However, the gene silencing effects mediated by dsRNA are repressed by interferon-induced global RNA degradation when the dsRNA size is larger than 25 base pairs (bp), especially in mammalian cells. Although transfection of short interfering RNA (siRNA) or microRNA (miRNA) of less than 21 bp can overcome interferon-associated problems, the size limitation impairs the usefulness of RNAi, as it is difficult to deliver such small and unstable dsRNAs in vivo due to high dsRNase activities in human bodies (Brantl (2002) Biochimica et Biophysica Acta 1575: 15-25). Therefore, there remains a need for a more effective and reliable gene modulation system.

SUMMARY

This invention is based, at least in part, on the discovery that an artificial intron can be used to regulate the function of a gene in a cell.

In one aspect, the invention features an isolated RNA comprising an intron RNA. The intron RNA is released in a cell (e.g., a mammalian cell), thereby modulating the function of a target gene. The isolated RNA does not contain a combination of a splice donor site that includes 5'-GU(A/G)AGU-3' and a splice acceptor site that includes 5'-CU(A/G)A(C/U)NG-3' (N is A, G, C, or U). It may contain a splice donor site that includes 5'-GUA(A/-)GAG(G/U)-3' ("-" designates an empty position), a splice acceptor site that includes 5'-G(A/U/-)(U/G)(C/G)C(U/C)(G/A)CAG-3' (SEQ ID NO:1), a branch site that includes 5'-UACU(A/U)A(C/U)(-/C)-3', a poly-pyrimidine tract that includes 5'-(U(C/U))$_{1-3}$(C/-)U$_{7-12}$C(C/-)-3' (SEQ ID NO:2) or 5'-(UC)$_{7-12}$NCUAG(G/-)-3' (SEQ ID NO:3), or a combination thereof. For example, the splice donor site can be 5'-AGGUAAGAGGAU-3' (SEQ ID NO:4), 5'-AGGUAAGAGU-3' (SEQ ID NO:5), 5'-AGGUA-GAGU-3', or 5'-AGGUAAGU-3'; the splice acceptor site can be 5'-GAUAUCCUGCAGG-3' (SEQ ID NO:6), 5'-GGCUG-CAGG-3', or 5'-CCACAGC-3'; and the branch site can be 5'-UACUAAC-3' or 5'-UACUUAUC-3'. The isolated RNA can be introduced into a cell for control of a gene function.

The invention also provides a DNA template for the isolated RNA of the invention, an expression vector comprising the DNA, a cultivated cell comprising the isolated RNA or the DNA, an animal (e.g., a mammal such as a mouse) comprising the isolated RNA or the DNA, and a composition comprising the isolated RNA or the DNA.

The invention further provides a method of producing an intron RNA. The method comprises cultivating the above-described cell to allow expression and/or release of the intron RNA. The released intron RNA can be left in the cell for control of a gene function, or be collected from the cell and used for generation of a DNA-RNA hybrid or delivery into another cell.

Also within the scope of the invention is a method of modulating the function of a target gene in a cell. The method comprises introducing into a cell an effective amount of the isolated RNA or DNA of the invention. The intron RNA is then released in the cell, thereby modulating the function of a target gene.

In another aspect, the invention features a composition comprising a chemokine (e.g., interleukin-2) and an isolated RNA or a DNA as described above. An effective amount of this composition can be administering into a cell (e.g., a mammalian cell or a cell infected by a virus) to modulate the function of a target gene. For example, an HIV-1-infected cell can be treated with a combination of interleukin-2 and an isolated RNA containing an intron RNA complementary to an HIV-1 genomic sequence. The intron RNA induces degradation of the HIV-1 genomic sequence or its derivatives, or prevent it from being translated into polypeptides.

In still another aspect, the invention features a composition comprising one or more agents that induce RNA-mediated modulation of the functions of two or more target genes in a cell (e.g., a mammalian cell or a cell infected by a virus). A method of modulating the functions of genes in a cell by administering into the cell an effective amount of the composition is also within the scope of the invention. For example, when a cell is infected by HIV-1, it can be treated With one or more DNA-RNA hybrids or exogenous intron RNAs that cause degradation of HIV-1 RNAs, cellular RNAs such as Naf1β, Nb2HP, and Tax1BP RNAs, or their derivatives, or prevent these RNAs from being translated into polypeptides.

The present invention provides compositions and methods for treating human diseases. Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting. Other features, objects, and advantages of the invention will be apparent from the description and the accompanying drawings, and from the claims.

BRIEF DESCRIPTION OF THE DRAWINGS

FIGS. 10A-B depict experimental evidence for generation of D-RNAi-induced miRNA.

DETAILED DESCRIPTION

Figure 1:
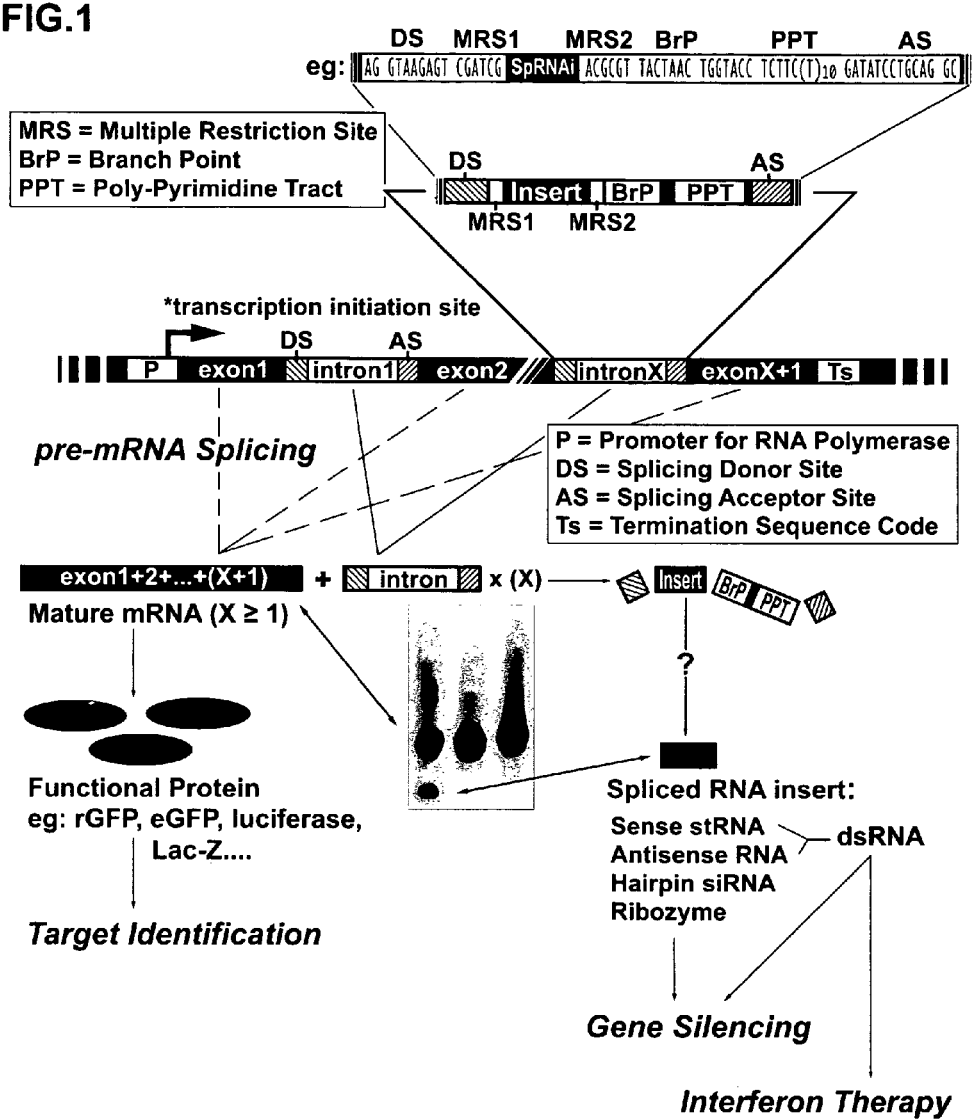
FIG. 1 depicts a novel strategy for producing desired RNA molecules in cells through RNA splicing. The exemplary sequence includes a donor site containing AG GTAAGAGT, a multiple restriction site 1 containing CGATCG, a multiple restriction site 2 containing ACGCGT, a branch point containing TACTAAC, a TGGTACC sequence, a poly-pyrimidine tract containing TCTTC(T)$_{10}$ (SEQ ID NO:29), and an acceptor site GATATCCTGCAG GC (SEQ ID NO:30).
Figure 2:
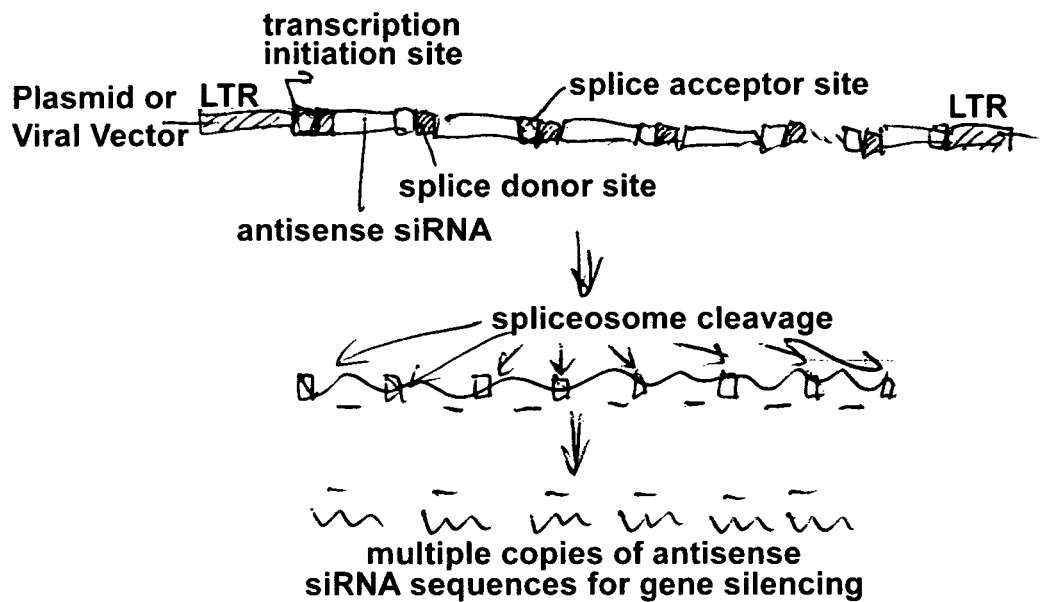
FIG. 2 depicts generation of antisense RNAs by spliceosome cleavage of retroviral (e.g., LTR) promoter-mediated precursor transcripts.
Figure 3:
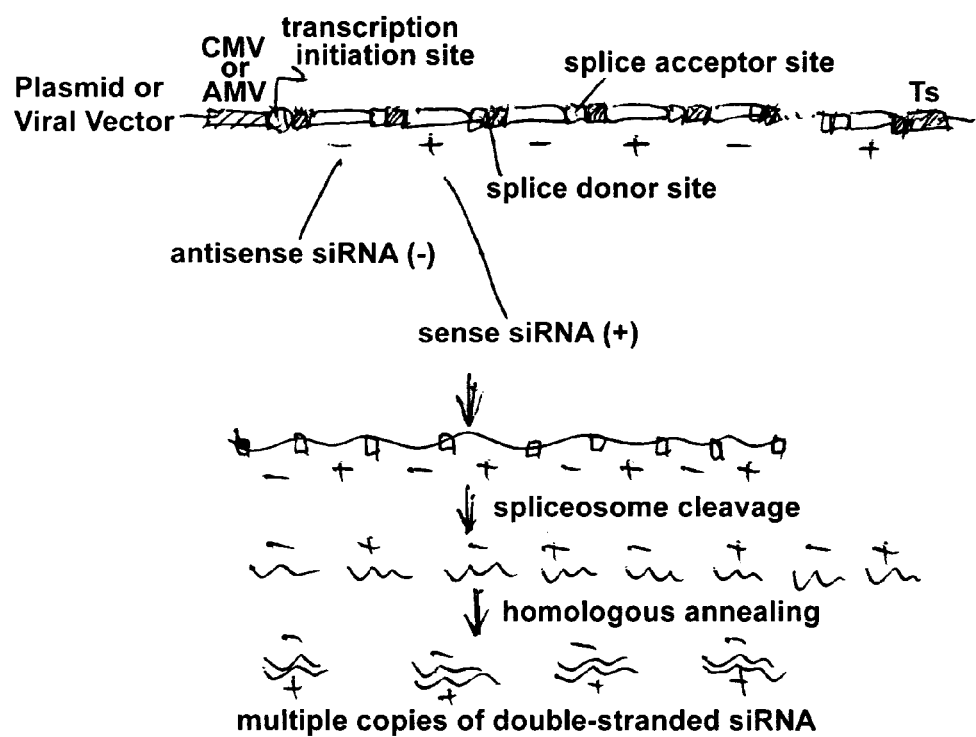
FIG. 3 depicts generation of sense and antisense siRNAs by spliceosome cleavage of viral (e.g., CMV or AMV) promoter-mediated precursor transcripts.
Figure 4:
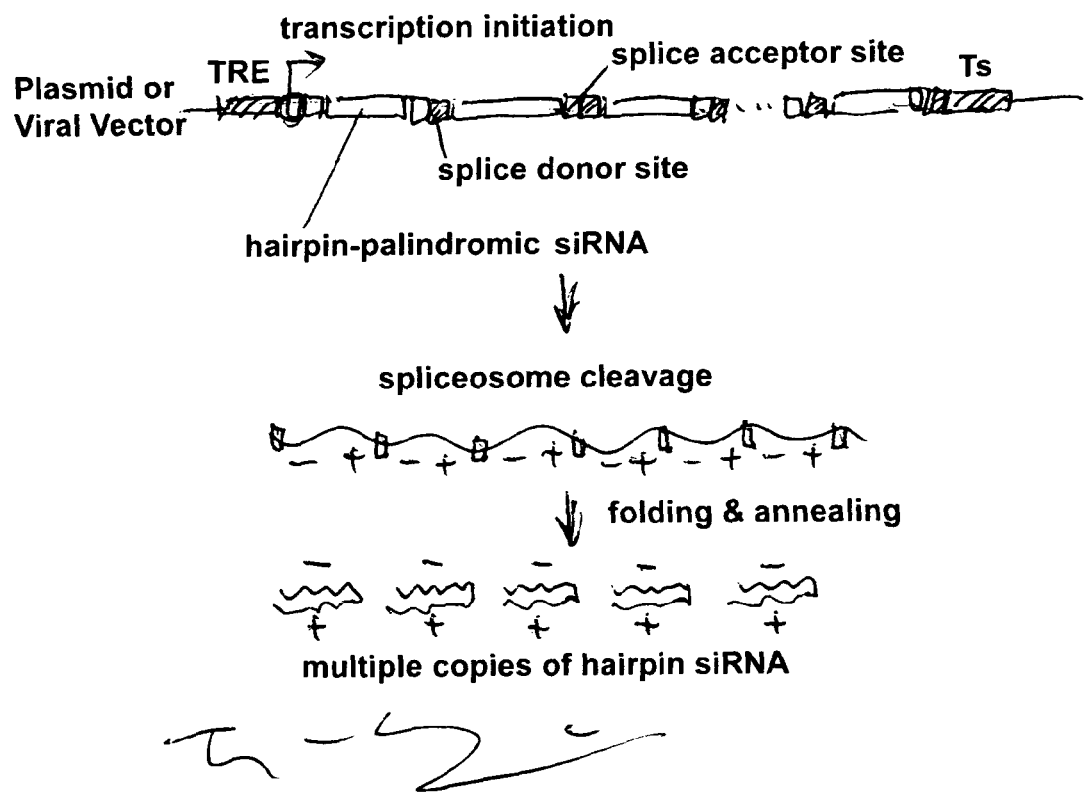
FIG. 4 depicts generation of hairpin RNAs by spliceosome cleavage of Pol II (e.g., TRE or Tet response element) promoter-mediated precursor transcripts.

This invention relates to RNA-mediated gene modulation. FIG. 1 shows an example of a novel strategy for producing a desired RNA molecule in a cell after RNA splicing event occurs. The desired RNA molecule, like a natural intron, is flanked by an RNA splicing donor and an acceptor site. The DNA template for the desired RNA is inserted into a gene, which is expressed by type-II RNA polymerase (Pol II) transcription machinery under the control of either Pol II or viral RNA promoter. Upon intracellular transcription, the transcript so produced is subjected to RNA splicing and/or processing events, thereby releasing the desired RNA molecule. In certain cases, the desired RNA molecule is an antisense RNA that serves as an antisense oligonucleotide probe for antisense gene therapy. In other cases, the desired RNA molecule is translated into a polypeptide that is useful in gene replacement therapy. The desired RNA molecule can also consist of small antisense and sense RNA fragments to function as double-stranded siRNA for RNAi induction. Moreover, the desired RNA molecule can be a small hairpin-like RNA capable of causing RNAi-associated gene silencing phenomena. In addition, the desired RNA molecule can also be a ribozyme. All of the above desired RNA molecules are produced by intracellular splicing events and therefore named as "SpRNAi" for convenience.

Accordingly, the invention features an isolated RNA comprising an intron RNA that is released in a cell, thereby modulating the function of a target gene. An "isolated RNA" is a ribonucleic acid the structure of which is not identical to that of any naturally occurring ribonucleic acid or to that of any fragment of a naturally occurring ribonucleic acid. A "funtion of a target gene" refers to the capability of the tareget gene to be transcribed into an RNA, the capability of the RNA to be stabilized, processed (e.g., through splicing), reverse transcribed or translated, and the capability of the RNA to play its normal role, e.g., serving as a tRNA and rRNA.

RNA splicing is a process that removes introns and joins exons in a primary transcript. The structures of intron RNAs are well known in the art. An intron usually contains signal sequences for splicing. For example, most introns start from the sequence GU and end with the sequence AG (in the 5' to 3' direction), which are referred to as the splice donor and splice acceptor site, respectively. In addition, an intron has a branch site between the donor and the acceptor site. The branch site contains an A residue (branch point), which is conserved in all genes. In many cases, the exon sequence is (A/C)AG at the 5'-exon-intron junction, and is G at the 3'-exon-intron junction. The fourth element is a poly-pyrimidine tract located between the branch site and the acceptor site.

In an isolated RNA of the invention, the splice donor site may contain 5'-GU.\(A/-)GAG(G/U)-3', the splice acceptor site may contain 5'-G(A/U/-)(U/G)(C/G)C(U/C)(G/A)CAG-3' (SEQ ID NO: 1), a branch site may contain 5'-UACU(A/U)A(C/U)(-/C)-3', and a poly-pyrimidine tract may contain 5'-(U(C/U))$_{1-3}$(C/-)U$_{7-12}$ C(C/-)-3'(SEQ ID NO: 2) or 5'-(UC)$_{7-12}$NCUAG(G/-)-3' (SEQ ID NO:3). Functionally equivalents of these sequences (e.g., sequences containing modified nucleotides) are included in the invention. The intron RNA serves as or is further processed to become, e.g., an RNA encoding a polypeptide, or an antisense RNA, short-temporary RNA (stRNA), microRNA (miRNA), small-interfering RNA (siRNA), short-hairpin RNA (shRNA), long deoxyribonucleotide-containing RNA (D -RNA), or ribozyme RNA, each of which may be in either sense or antisense orientation. Design of antisense RNA, stRNA, miRNA, siRNA, shRNA, D-RNA and ribozyme RNA is well known in the art. The intron RNA region homologous or complementary to its target gene ranges from 14 to 2,000 nucleotides, most preferably between 19 and 500 nucleotides. The intron RNA may be 35-100% (i.e., any integral between and including 35 and 100) identical or complementary to its target gene. The preferred homology or complementarity is 35-65% and more preferably 41-49% for an shRNA, 40-100% and more preferably 90-100% for a sense or antisense RNA. The length of an siRNA/miRNA/shRNA may be 16-38 nucleotides, and preferably 19-25 nucleotides. Additionally, there may be one or more linker sequences, e.g., between the donor and the acceptor site and the antisense RNA, stRNA, siRNA, shRNA, D-RNA or ribozyme RNA sequence. The isolated RNA may further contain exons encoding a polypeptide for co-expression with the intron RNA. The polypeptide may be a normal protein, a missing protein, a dominant-negative protein, or a protein marker such as a fluorescent protein, luciferase, or lac-Z.

An isolated RNA of the invention can be chemically synthesized or produced by transcription from a DNA template in vitro and in vivo. The template DNA can be cloned into an expression vector according the methods well known in the art. Examples of such vectors include, but are not limited to, plasmids, cosmids, phagemids, yeast artificial chromosome, retroviral vectors, lentiviral vectors, lambda vector, adenoviral (AMV) vector, adeno-associated viral (AAV) vector, hepatitis virus (HBV)-modified vector, and cytomegalovirus (CMV)-related viral vector.

The isolated RNA, DNA template, and expression vector described above can be introduced into a cultured cell or a subject (e.g., an animal or a human) using methods commonly employed in the art such as transfection, infection, eletroporation, micro-injection, and gene-gun penetration. To help with the delivery into a cell, the isolated RNA, DNA template, and expression vector may be formulated into a composition. The intron RNA, once expressed and/or released in the cell, can modulate the function of a target gene, for example, inhibit a cancer-related gene, potential viral gene, and microbe-related gene. Therefore, this emthod is useful for treating and preventing diseases such as cancer and viral or microbal infection.

In one in vivo approach, a composition is suspended in a pharmaceutically acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 µg/kg. Wide variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, the composition may be delivered to the subject, for example, by use of polymeric, biodegradable microparticle or microcapsule delivery devices known in the art.

Another way to achieve uptake of the nucleic acid is to use liposomes, prepared according to standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995) *J. Mol. Med.* 73: 479). Furthermore, tissue specific targeting can be achieved by use of tissue-specific transcriptional regulatory elements (TRE) which are known in the art. Delivery of naked nucleic acids (i.e., without a delivery vehicle) to an intramuscular, intradermal, or subcutaneous site is another means to achieve in vivo expression.

An "effective amount" is an amount of the compound or composition that is capable of producing a medically desirable result (e.g., a decreased expression level of a cancer-related gene, potential viral gene, or microbe-related gene) in a treated subject.

In particular, an animal comprising an isolated RNA or a DNA of the invention can be produced according to the methods described above or any other methods known in the art. For example, a "knock-out animal" may be generated in which a target gene is partially (e.g., only in some tissues) or completely inhibited. The animal can be a farm animal such as a pig, goat, sheep, cow, horse and rabbit, a rodent such as a rat, guinea pig, and mouse, or a non-human primate such as a baboon, monkey, and chimpanzee.

These animals of the invention can be used as disease models. In particular, these animals can be used to identify a compound or composition effective for treatment or prevention of a disease. Compounds or compositions can be identified by administering a test compound or composition to a model animal or by contacting the test compound or composition with an organ, a tissue or cells derived from a model animal. Effects of the test compound or composition on the disease of the animal, organ, tissue or cells are evaluated. Test compounds or compositions that palliate the disease symptoms can be effective for treatment or prevention of the disease.

A second aspect of the invention is based on the discovery that the combination of interleukin-2 and a viral RNA-antisense DNA hybrid significantly reduced human immunodeficiency virus-1 (HIV-1) subtype B gene activity. Consequently, the invention features a composition comprising a chemokine and an isolated RNA or a DNA of the invention. The isolated RNA or DNA allows an intron RNA to be released in a cell, thereby modulating the function of a target gene. Examples of chemokines include, but are not limited to, interleukin-2 (IL-2), interleukin-10 (IL-10), interleukin-17 (IL-17), tumor narcosis factor-α (TNF-α), and tumor narcosis factor-β (TNF-β). The intron RNA may contain, e.g., an antisense RNA, stRNA, miRNA, siRNA, shRNA, D-RNA, or ribozyme RNA. The composition can be administering into a cell according to the methods described above for modulating the function of a target gene in a cell, e.g., inducing degradation of an HIV-1 genomic sequence or preventing an HIV-1 genomic sequence from being translated into a polypeptide in an HIV-1 infected cell.

It was also found that SpRNAi-induced silencing of cellular genes Naf1β, Nb2HP and Tax1BP prevents HIV-1 type B infection. The invention therefore provides a composition comprising one or more agents (e.g., an antisense RNA, stRNA, miRNA, siRNA, shRNA, D-RNA, SpRNAi, ribozyme RNA, or a combination thereof) that induce RNA-mediated modulation of the functions of two or more target genes in a cell. The composition can be administering into a cell according to the methods described above for control of the functions of genes.

Applications of the present invention include, without limitation, therapy by suppression of cancer-related genes, vaccination against potential viral genes, treatment of microbe-related genes, research of candidate molecular pathways with systematic knockout/knockdown of involved molecules, and high-throughput screening of gene functions based on microarray analysis. The present invention can also be used as a tool for studying gene function under physiological and therapeutical conditions, providing compositions and methods for altering the characteristics of eukaryotic cells such as cancerous, virus-infected, microbe-infected, physiologically diseased, genetically mutated, and pathogenic cells.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLES

1. Cell Culture and Treatment

Rat neuronal stem cell clones AP31 and PZ5a were primary-cultured and maintained as described by Palmer et al. (1999) *J. Neuroscience* 19: 8487-8497. The cells were grown on polyornathine/laminin-coated dishes in DMEM/F-12

(1:1; high glucose) medium containing 1 mM·L-glutamine supplemented with 1×N2 supplements (Gibco/BRL, Gaithersburg, Md.) and 20 ng/ml FGF-2 (Invitrogen, Carlsbad, Calif.) without serum at 37° C. under 5% $CO_2$. For long-term primary cultures, 75% of the medium was replaced with new growth medium every 48 h. Cultures were passaged at ~80% confluency by exposing the cells to trypsin-EDTA solution (Irvine Scientific) for 1 min and rinsing them once with DMEM/F-12. Detached cells were replated at 1:10 dilution in fresh growth medium supplemented with 30% (v/v) conditioned medium which had been exposed to cells for 24 h before passaging. Human prostatic cancer LNCaP cells were obtained from American Type Culture Collection (ATCC, Rockville, Md.) and grown in RPMI 1640 medium supplemented with 10% fetal bovine serum with 100 µg/ml gentamycin at 37° C. under 10% $CO_2$. The LNCaP culture was passaged at ~80% confluency by exposing cells to trypsin-EDTA solution for 1 min and rinsing them once with RPMI, and detached cells were replated at 1:10 dilution in fresh growth medium. After a 48-hour incubation period, RNA was isolated from the cells using RNeasy spin columns (Qiagen, Valencia, Calif.), fractionated on a 1% formaldehyde-agarose gel, and transferred onto nylon membranes. The genomic DNA was also isolated using apoptotic DNA ladder kit (Roche Biochemicals, Indianapolis, Ind.) and assessed by 2% agarose gel electrophoresis, while cell growth and morphology were examined using microscopy and cell counting.

2. Construction of SpRNAi-containing Genes

Synthetic nucleic acid sequences used for generation of three different SpRNAi introns containing either sense, antisense or hairpin eGFP insert were as follows: N1-sense, 5'-pGTAAGAGGAT CCGATCGCAG GAGCGCACCA TCTTCTTCAA GA-3' (SEQ ID NO:7); N1-antisense, 5'-pCGCGTCTTGA AGAAGATGGT GCGCTCCTGC GATCGGATCC TCTTAC-3' (SEQ ID NO:8); N2-sense, 5'-pGTAAGAGGAT CCGATCGCTT GAAGAAGATG GTGCGCTCCT GA-3' (SEQ ID NO:9); N2-antisense, 5'-pCGCGTCAGGA GCGCACCATC TTCTTCAAGC GATCGGATCC TCTTAC-3' (SEQ ID NO:10); N3-sense, 5'-pGTAAGAGGAT CCGATCGCAG GAGCGCACCA TCTTCTTCAA GTTAACTTGA AGAAGATGGT GCGCTCCTGA-3' (SEQ ID NO:11); N3-antisense, 5'-pCGCGTCAGGA GCGCACCATC TTCTTCAAGT TAACTTGAAG AAGATGGTGC GCTCCTGCGA TCGGATCCTC TTAC-3' (SEQ ID NO:12); N4-sense, 5'-pCGCGTTACTA ACTGGTACCT CTTCTTTTTT TTTTTGATAT CCTGCAG-3' (SEQ ID NO:13); N4-antisense, 5'-pGTCCTGCAGG ATATCAAAAA AAAAAGAAGA GGTACCAGTT AGTAA-3' (SEQ ID NO:14). Additionally, two exon fragments were generated by DraII restriction enzyme cleavage of red fluorescent rGFP gene at nucleotide (nt) 208, and the 5' fragment was further blunt-ended using T4 DNA polymerase. The rGFP refers to a new red-fluorescin chromoprotein generated by insertion of an additional aspartate at amino acid (aa) 69 of HcRed1 chromoprotein from *Heteractis crispa*. (Gurskaya et al. (2001) *FEBS Letters* 507: 16-20), developing less aggregate and almost twice intense far-red fluorescent emission at ~570-nm wavelength. This mutated rGFP gene sequence was cloned into pHcRed1-N1/1 plasmid vector (BD Biosciences) and propagated in *E. coli* DH5α in LB medium containing 50 µg/ml kanamycin (Sigma). The pHcRed1-N1/1 plasmid was cleaved with XhoI and XbaI restriction enzymes. A 769-bp rGFP fragment and a 3,934-bp empty plasmid were purified separately from a 2% agarose gel after electrophoresis.

Hybridization of N1-sense to N1-antisense, N2-sense to N2-antisense, N3-sense to N3-antisense, and N4-sense to N4-antisense was separately performed by heating each mixture of complementary sense and antisense (1:1) sequences to 94° C. for 2 min and then 70° C. for 10 min in 1×PCR buffer (e.g., 50 mM Tris-HCl, pH 9.2 at 25° C., 16 mM $(NH_4)_2SO_4$, 1.75 mM $MgCl_2$). Subsequently, ligation of the N1, N2 or N3 hybrid to the N4 hybrid was performed by gradually cooling a mixture of N1-N4, N2-N4 or N3-N4 (1:1) hybrids from 50° C. to 10° C. over a period of 1 h, and then $T_4$ ligase and buffer (Roche) were mixed with the mixture for 12 h at 12° C. so as to obtain introns for linking to exons with proper ends. After the rGFP exon fragments were added into the reaction (1:1:1), T4 ligase and buffer were adjusted accordingly for continued ligation for another 12 h at 12° C. For cloning the right sized recombinant rGFP gene, 10 ng of the ligated nucleotide sequences were amplified by PCR with rGFP-specific primers 5'-dCTCGAGCATG GTGAGCGGCC TGCTGAA-3' (SEQ ID NO:15) and 5'-dTCTAGAAGTT GGCCTTCTCG GGCAGGT-3' (SEQ ID NO:16) at 94° C., 1 min; 52° C., 1 min; and then 68° C., 2 min for 30 cycles. The PCR products were fractionated on a 2% agarose gel, and a ~900-bp nucleotide sequence was extracted and purified using a gel extraction kit (Qiagen). The composition of this ~900 bp SpRNAi-eGFP-containing rGFP gene was confirmed by sequencing.

3. Cloning of SpRNAi-containing Genes into Various Vectors

Since the recombinant gene possesses an XhoI and an XbaI restriction site at its 5'- and 3'-end, respectively, it can be easily cloned into a vector with ends complementary to the XhoI and XbaI sites. The vector can be an expression vector, e.g., a plasmid, cosmid, phagmid, yeast artificial chromosome, or viral vector. Moreover, since the insert within the intron is flanked by a PvuI and an MluI restriction site at its 5'- and 3'-end, respectively, the insert can be removed and replaced with another insert with ends complementary to the PvuI and MluI sites. The insert sequence can be homologous or complementary to a gene fragment such as a fluorescent protein gene, luciferase gene, lac-Z gene, plant gene, viral genome, bacterial gene, animal gene, and human oncogene. The homology and/or complementarity ranges from about 30~100%, more preferably 35~49% for a hairpin-shRNA insert and 90~100% for both sense-siRNA and antisense-siRNA inserts.

For cloning into plasmids, the SpRNAi-recombinant rGFP gene and the linearized 3,934-bp empty pHcRed1-N1/1 plasmid were mixed at 1:16 (w/w) ratio. The mixture was cooled from 65° C. to 15° C. over a period of 50 min, and then $T_4$ ligase and buffer were added into the mixture for ligation at 12° C. for 12 h. A so formed SpRNAi-recombinant rGFP-expressing plasmid vector was propagated in *E. coli* DH5α in LB medium containing 50 µg/ml kanamycin. A positive clone was confirmed by PCR with rGFP-specific primers SEQ ID NO:15 and SEQ ID NO:16 at 94° C., 1 min and then 68° C., 2 min for 30 cycles and subsequent sequencing. For cloning into viral vectors, the same ligation procedure was performed except that an XhoI/XbaI-linearized pLNCX2 retroviral vector (BD Biosciences) was used. The eGFP insert within the SpRNAi intron was removed and replaced with various integrin β1-specific insert sequences with ends complementary to the PvuI and MluI sites.

Synthetic nucleic acid sequences used for generation of various SpRNAi introns containing either sense, antisense or hairpin integrin β1 insert were as follows: P1-sense, 5'-pCG-CAAGCAGG GCCAAATTGT GGGTA-3' (SEQ ID NO:17); P1-antisense, 5'-pTAGCACCCAC AATTTGGCCC TGCTTGTGCG C-3' (SEQ ID NO:18); P2-sense, 5'-pC-GACCCACAA TTTGGCCCTG CTTGA-3' (SEQ ID NO:19); P2-antisense, 5'-pTAGCCAAGCA GGGC-CAAATT GTGGGTTGCG C-3' (SEQ ID NO:20); P3-sense, 5'-pCGCAAGCAGG GCCAAATTGT GGGTTTAAAC CCACAATTTG GCCCTGCTTG A-3' (SEQ ID NO:21); P3-antisense, 5'-pTAGCACCCAC AATTTGGCCC TGCT-TGAATT CAAGCAGGGC CAAATTGTGG GTTGCGC (SEQ ID NO:22). These inserts were designed using Gene Runner software v3.0 (Hastings, Calif.) and formed by hybridization of P1-sense to P1-antisense, P2-sense to P2-antisense and P3-sense to P3-antisense for targeting nt 244~265 of the integrin β1 gene (GenBank Access No. NM 002211.2). The SpRNAi-containing rGFP-expressing retroviral vector was propagated in *E. coli* DH5α in LB medium containing 100 µg/ml ampcillin (Sigma). A packaging cell line PT67 (BD Biosciences) was also used for producing infectious, replication-incompetent viruses. Transfected PT67 cells were grown in DMEM medium supplemented with 10% fetal bovine serum with 4 mM L-glutamine, 1 mM sodium pyruvate, 100 µg/ml streptomycin sulfate and 50 µg/ml neomycin (Sigma) at 37° C. under 5% $CO_2$. The titer of the virus produced by PT67 cells was determined to be at least $10^6$ cfu/ml before transfection.

4. Low Stringency Northern Blot Analysis

RNA (20 µg total RNA or 2 µg poly[$A^+$] RNA) was fractionated on 1% formaldehyde-agarose gels and transferred onto nylon membranes (Schleicher & Schuell, Keene, N.H.). A synthetic 75-bp probe (5'-dCCTGGCCCCC TGCTGC-GAGT ACGGCAGCAG GACGTAAGAG GATCCGATCG CAGGAGCGCA CCATCTTCTT CAAGT-3' (SEQ ID NO:23)) targeting the junction region between rGFP and the hairpin eGFP-insert was labeled with the Prime-It II kit (Stratagene, La Jolla, Calif.) by random primer extension in the presence of [$^{32}$P]-dATP (>3000 Ci/mM, Amersham International, Arlington Heights, Ill.), and purified using 30 bp-cutoff Micro Bio-Spin chromatography columns (Bio-Rad, Hercules, Calif.). Hybridization was carried out in a mixture of 50% freshly deionized formamide (pH 7.0), 5× Denhardt's solution, 0.5% SDS, 4×SSPE and 250 mg/mL denatured salmon sperm DNAs (18 h, 42° C.). Membranes were sequentially washed twice in 2×SSC, 0.1% SDS (15 min, 25° C.), and once in 0.2×SSC, 0.1% SDS (15 min, 25° C.) before autoradiography.

5. Suppression of Specific Gene Expression

For interference with eGFP expression, rat neuronal stem cells were transfected with SpRNAi-recombinant rGFP plasmids encoding either a sense, antisense or hairpin eGFP insert using Fugene reagent (Roche). Plasmids containing insert-free rGFP gene and SpRNAi-recombinant rGFP gene with an insert against HIV-gag p24 were used as negative controls. Cell morphology and fluorescent images were photographed at 0-, 24- and 48-hour time points after transfection. At the 48-h incubation time point, the rGFP-positive cells were sorted by flow cytometry and collected for Western blot analysis. For interference with integrin β1 expression, LNCaP cells were transfected with pLNCX2 retroviral vectors containing various SpRNAi-recombinant rGFP genes against nt 244~265 of integrin β1 using the Fugene reagent. The transfection rate of pLNCX2 retroviral vector into LNCaP cells was determined to be about 20%, while the pLNCX2 virus was less infectious to LNCaP cells. The same analyses were performed as aforementioned.

6. SDS-PAGE and Western Blot Analysis

For immunoblotting, cells were rinsed with ice-cold PBS after the growth medium was removed, and then treated with the CelLytic-M lysis/extraction reagent (Sigma Chemical, St. Louis, Mo.) supplemented with protease inhibitors, Leupeptin, TLCK, TAME and PMSF following manufacturer's recommendations. The cells were incubated at room temperature on a shaker for 15 min, scraped into microtubes, and centrifuged for 5 min at 12,000×g to pellet the cell debris. Protein-containing cell lysate was collected and stored at −70° C. until use. Protein concentrations were determined as described (Bradford (1976) *Anal. Biochem.* 72: 248-254) using SOFT-max software package on an E-max microplate reader (Molecular Devices, Sunnyvale, Calif.). 30 µg of cell lysate was added into SDS-PAGE sample buffer either with (reduced) or without (unreduced) 50 mM DTT, and boiled for 3 min before loading onto 8% polyacylamide gels, while the reference lane was loaded with 2~3 µl molecular weight markers (BioRad). SDS-polyacrylamide gel electrophoresis was performed according to the standard protocols (Sambrook and Russell, *Molecular Cloning*, 3rd Ed., (2001) Cold Spring Harbor Laboratory Press: New York). Protein fractions were electroblotted onto a nitrocellulose membrane, blocked with Odyssey blocking reagent (Li-Cor Biosciences, Lincoln, NB) for 1~2 h at room temperature. GFP expression was assessed using primary antibodies directed against eGFP (1:5,000; JL-8, BD Biosciences, Palo Alto, Calif.) or rGFP (1:10,000; BD Biosciences) overnight at 4° C. The blot was then rinsed 3 times with TBS-T and exposed to a secondary antibody, goat anti-mouse IgG conjugate with Alexa Fluor 680 reactive dye (1:2,000; Molecular Probes), for 1 h at room temperature. After three more TBS-T rinses, scanning and image analysis were performed using Li-Cor Odyssey Infrared Imager and Odyssey Software v.10 (Li-Cor). For integrin β1 analysis, the same procedure was performed except that primary antibodies directed against integrin β1 (1:2,000; LM534, Chemicon, Temecula, Calif.) were used.

7. In Vitro Generation of Deoxyribonucleotidylated RNA Probes

The RNA-polymerase cycling reaction (RNA-PCR) procedure can be modified to synthesize mRNA-aDNA and/or mDNA-aRNA hybrids (Lin et al. (1999) *Nucleic Acids Res.* 27, 4585-4589) from an SpRNAi-recombinant gene, expression-competent vector template or transcriptome source. As an example of using an SpRNAi-recombinant gene source, an SpRNAi-sense HIV recombinant gene containing a sequence homologues to HIV-1 genome from +2113 to +2453 bases was generated following a procedure similar to Section 2 above. The RNA product (10~50 µg) of the SpRNAi-sense HIV recombinant gene were transcribed in about $10^6$ transfected cells, isolated using RNeasy columns (Qiagen), and then hybridized to its pre-synthesized complementary DNA (cDNA) by heating and then cooling the mixture from 65° C. to 15° C. over a period of 50 min. Transfection was performed following the same procedure shown in Section 5 above.

8. Design of Artificially Recombined Genes for Splicing-directed Gene Silencing

RNA splicing/processing-directed gene silencing was tested using an artificial recombinant gene, SpRNAi-rGFP (FIG. 1). A DNA template for a splicing-competent intron (SpRNAi) was inserted into an intron-free red fluorescin gene (rGFP), providing splicing-directed gene silencing effects through pre-mRNA splicing and some unknown processing mechanisms. Although a model of gene silencing through pre-mRNA splicing is shown here, the same principle can be used for the design of gene silencing inserts working through other pre-RNA processing, e.g., pre-ribosomal RNA (pre-rRNA)-processing, which is mainly mediated by type-I RNA polymerase (Pol I) transcription machinery. The splicing-competent intron is flanked by a donor (DS) and an acceptor (AS) splicing site, and contains at least one gene homologue insert, branch point (BrP) and poly-pyrimidine tract (PPT) inbetween the DS-AS sites for interacting with spliceosome machinery. Using low stringency Northern blotting (mid-bottom of FIG. 1), 15~45 bp intron-insert fragments were seen to be released from the SpRNAi-rGFP gene transcript (left), rather than an intron-free rGFP (middle) or a defective SpRNAi-rGFP (right) RNA without a functional splice donor site, while the spliced exons were linked to form a mature RNA for rGFP protein synthesis. The "?" mark in FIG. 1 indicates an unknown mechanism for processing of a ~120-bp intron, resulting in small interfering intron-insert fragments. Short sense, short antisense and hairpin constructs of some gene homologue inserts were successfully tested for inducing specific gene silencing in various cell types.

As shown in FIG. 1, DNA templates for splicing-competent introns (SpRNAi) were synthesized and inserted into an intron-free red fluorescin gene (rGFP) that was mutated from the HcRed1 chromoprotein of Heteractis crispa. Since the inserted intron disrupted the functional fluorescin structure of the rGFP protein, occurrence of intron splicing and rGFP-mRNA maturation was indicated by the reappearance of red fluorescent light emission at the 570-nm wavelength in a transfected cell. Construction of SpRNAi was based on the natural structure of a pre-messenger RNA intron, consisting of spliceosome-dependent nucleotide components, such as donor and acceptor splicing sites in both ends for precise cleavage, branch point domain for splicing recognition, poly-pyrimidine tract for spliceosome interaction, linkers for connection of each major components and some artificially added multiple restriction/cloning sites for cloning of inserts. Based on prior studies, the donor splicing site is an oligonucleotide sequence either containing or homologous to 5'-exon-AG-(splicing point)-GTA(A/-)GAG(G/T)-3' (SEQ ID NO:24), e.g., 5'-AG GTAAGAGGAT-3' (SEQ ID NO:25), 5'-AG GTAAGAGT-3' (SEQ ID NO:26), 5'-AG GTAGAGT-3', 5'-AG GTAAGT-3' and so on. The acceptor splicing site is an oligonucleotide sequence either containing or homologous to 5'-G(W/-)(T/G)(C/G)C(T/C)(G/A)CAG-(splicing point)-G/C-exon-3' (while W is a pyrimidine, i.e., A or T) (SEQ ID NO:27), e.g., 5'-GATATCCTGCAG G-3' (SEQ ID NO:28), 5'-GGCTGCAG G-3', 5'-CCACAG C-3' and so on. The branch point is an "A" residue located within a sequence homologous to 5'-TACT(A/T)A*(C/T)(-/C)-3' (while the symbol "*" marks the branch site), e.g., 5'-TACTAAC-3', 5'-TACTTATC-3' and so on. The poly-pyrimidine tract is a high T and/or C content oligonucleotide sequence homologous to 5'-(TY)m(C/-)(T)nC(C/-)-3' (SEQ ID NO:31) or 5'-(TC)nNCTAG(G/-) -3' (while Y is a C or T) (SEQ ID NO:32). The symbols "m" and "n" indicate the numbers of repeats, preferably, m=1~3 and n=7~12. For all the above splicing components, the deoxythymidine (T) in a DNA template is replaced by uridine (U) after transcription.

To test the function of a spliced intron, various inserts were cloned into SpRNAi through multiple restriction/cloning sites, e.g., those for AatII, AccI, AflII/III, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/U1/XI, ClaI, Csp6I, DpnI, DraI/II, EagI, Ecl136II, EcoRI/RII/47III, EheI, FspI, HaeIII, HhaI, HinPI, HindIII, HinfI, HpaI/II, KasI, KpnI, MaeII/III, MfeI, MluI, MscI, MseI, NaeI, NarI, NcoI, NdeI, NgoMI, NotI, NruI, NsiI, PmlI, Ppu10I, PstI, PvuI/II, RsaI, SacI/II, SalI, Sau3AI, SmaI, SnaBI, SphI, SspI, StuI, TaiI, TaqI, XbaI, XhoI and/or XmaI endonucleases. These inserts are DNA templates for aberrant RNAs, e.g., short-temporary RNA (stRNA), small-interfering RNA (siRNA), short-hairpin RNA (shRNA), long deoxyribonucleotide-containing RNA (D-RNA) and potentially ribozyme RNA in either sense or antisense orientation. As demonstrated in the examples below, the gene silencing effect of a hairpin-RNA-containing SpRNAi is stronger than that of a sense- and antisense-RNA-containing SpRNAi, showing an average of >80% knockdown specificity to all targeted gene products. Such knockdown specificity is mainly determined by the homologous or complementary region of an insert to the targeted gene transcript. For example, the tested hairpin-SpRNAi insert had about 40~42% homology and another 40~42% complementarity to the targeted gene domain, within-in-between of which an A/T-rich linker sequence filled in the rest 8~10% space. For the less potent sense- and antisense-SpRNAi inserts, although the homology or complementarity can be increased up to 100%, an average of 40~50% knockdown efficacy was detected in most of the transfection tests. Thus, different types of SpRNAi inserts and/or the combination thereof can be used to manipulate specific gene expression levels in cells.

9. Simultaneous Expression of rGFP and Silencing of eGFP by SpRNAi Transfection

For the convenience of gene delivery and activation in cells, SpRNAi-containing genes were cloned into an expression-competent vector, e.g., plasmid, cosmid, phagmid, yeast artificial chromosome, viral vector and so on. As shown in FIGS. 1-4, the vectors can contain at least one viral or type-II RNA polymerase (Pol II) promoter or both for the expressing of the SpRNAi-gene in eukaryotic cells, a Kozak consensus translation initiation site to increase translation efficiency in eukaryotic cells, SV40 polyadenylation signals downstream of the SpRNAi-gene for processing of the 3'-end gene transcript, a pUC origin of replication for propagation in prokaryotic cells, at least two multiple restriction/cloning sites for cloning of the SpRNAi-gene, an optional SV40 origin for replication in mammalian cells expressing the SV40 T antigen and an optional SV40 early promoter for expressing an antibiotic resistance gene in replication-competent prokaryotic cells. The expression of antibiotic resistance genes was used as a selective marker for searching of successfully transfected or infected clones that are resistance to the antibiotics such as penicillin G, ampcillin, neomycin, paromycin, kanamycin, streptomycin, erythromycin, spectromycin, phophomycin, tetracycline, rifapicin, amphotericin B, gentamicin, chloramphenicol, cephalothin, tylosin and the combination thereof. The vector was therefore stable enough to be introduced into a cell(s), tissue or animal body using a highly efficient gene delivery method, e.g., liposomal transfection, chemical transfection, chemical transformation, electroporation, infection, micro-injection and gene-gun penetration.

Figure 5:
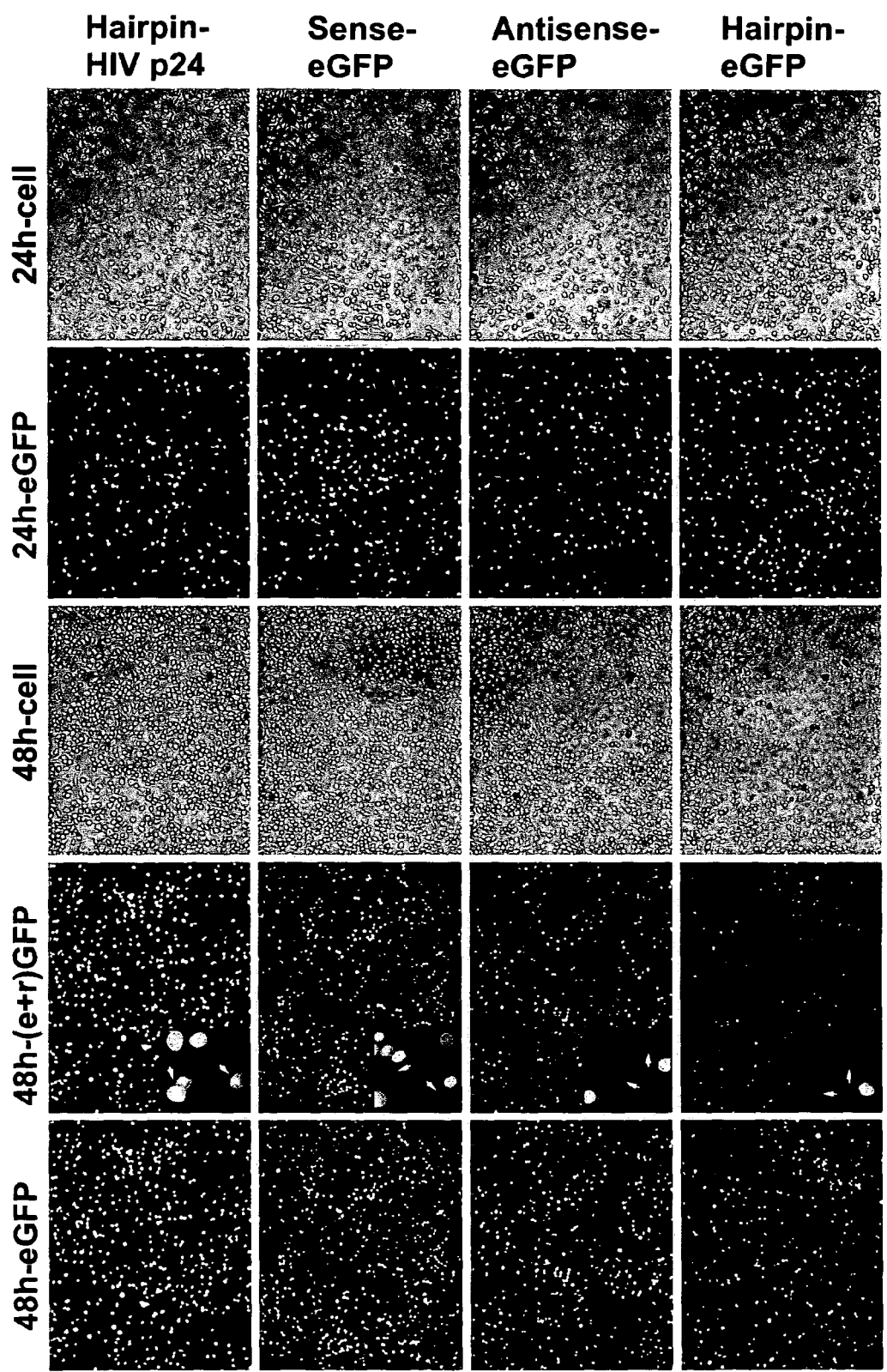
FIG. 5 depicts microscopic results, showing interference with green fluorescent protein (eGFP) expression in rat neuronal stem cells by various SpRNAi constructs.

As shown in FIG. 5, transfection of the plasmids described in Sections 2 and 3 (containing various SpRNAi-rGFP recombinant genes against the expression of a commercially available Aequorea victoria green fluorescent protein (eGFP)) was found to be successful in both expression of rGFP (red) and silencing eGFP (green). The use of eGFP-positive rat neuronal stem cell clones provided an excellent visual aid to measure the silencing effects of various SpRNAi inserts. Rat neuronal stem cell clones AP31 and PZ5a were primary-cultured and maintained as described in Section 1. 24-h after transfection, almost the same amount of total cell number and eGFP-positive cell population were well seeded and very limited apoptotic or differentiated cells occurred. Silencing of eGFP emission at the 518-nm wavelength was detected 36~48 hours after transfection, indicating a potential onset timing required for the release of small interfering inserts from SpRNAi-rGFP gene transcripts by spliceosome machinery. Since all successfully transfected cells displayed red fluorescent emission at about 570-nm wavelength, the gene silencing effect was traced by measuring relative light intensity of the green fluorescent emission in the red fluorescent cells, showing a knockdown potency of hairpin-eGFP>>sense-eGFP~ antisense-eGFP>>hairpin-HIV p24 (negative control) insert.

10. Western Blot Analysis of RNA Splicing/processing-directed eGFP Silencing

Figure 6:
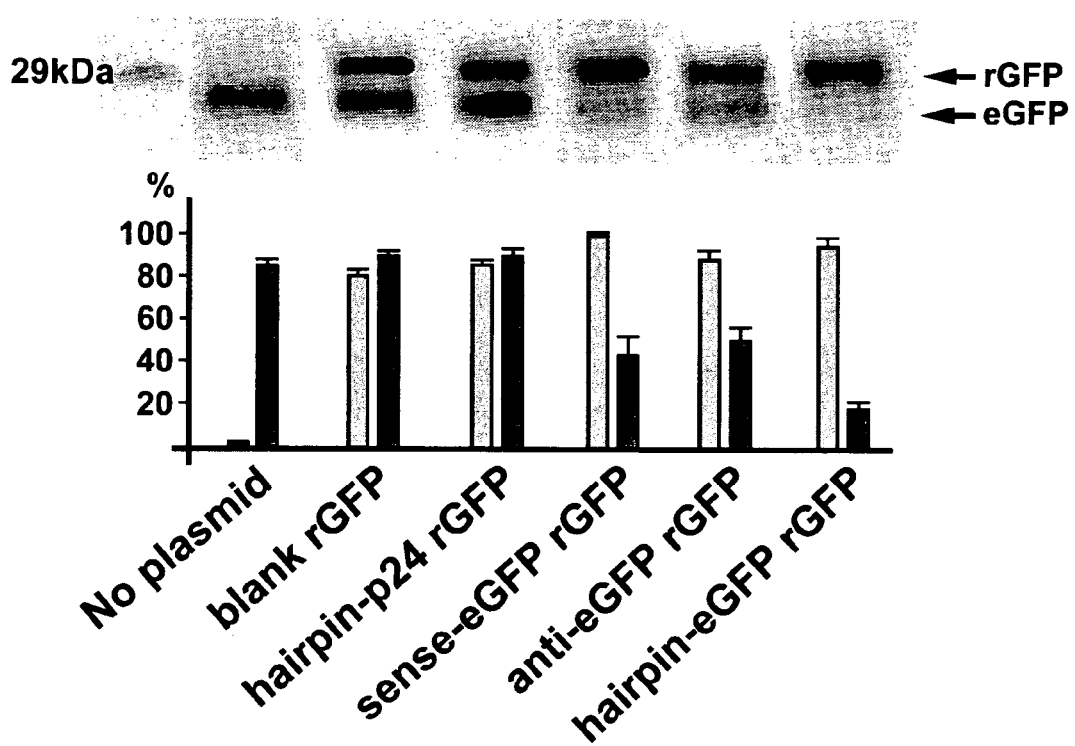
FIG. 6 depicts Western blot results, showing interference with green fluorescent protein (eGFP) expression in rat neuronal stem cells by various SpRNAi constructs.

As shown in FIG. 6, knockdown levels of eGFP protein in rat neuronal stem cell clones AP31 and PZ5a by various SpRNAi inserts were measured on an unreduced 6% SDS-polyacrylamide gel. To normalize the loading amounts of transfected cellular proteins, rGFP protein levels (~30 kDa, red bars) were adjusted to be comparatively equal, representing an average expression range of 82-100% intensity (Y axis). The eGFP levels (27 kDa, green bars) were found to be reduced by transfection of SpRNAi-rGFP genes containing sense-eGFP (43.6%), antisense-eGFP (49.8%) or hairpin-eGFP (19.0%) inserts, but not that of intron-free rGFP gene (blank control) or SpRNAi-rGFP gene containing hairpin-HIV p24 insert (negative control). These findings confirm the knockdown potency of hairpin-eGFP>>sense-eGFP~ antisense-eGFP>>hairpin-HIV p24 (negative control), and also demonstrate that only a gene insert which is either homologous or complementary (or partially homologous or complementary) to the targeted gene can elicit this gene-specific silencing effect.

Figure 7:
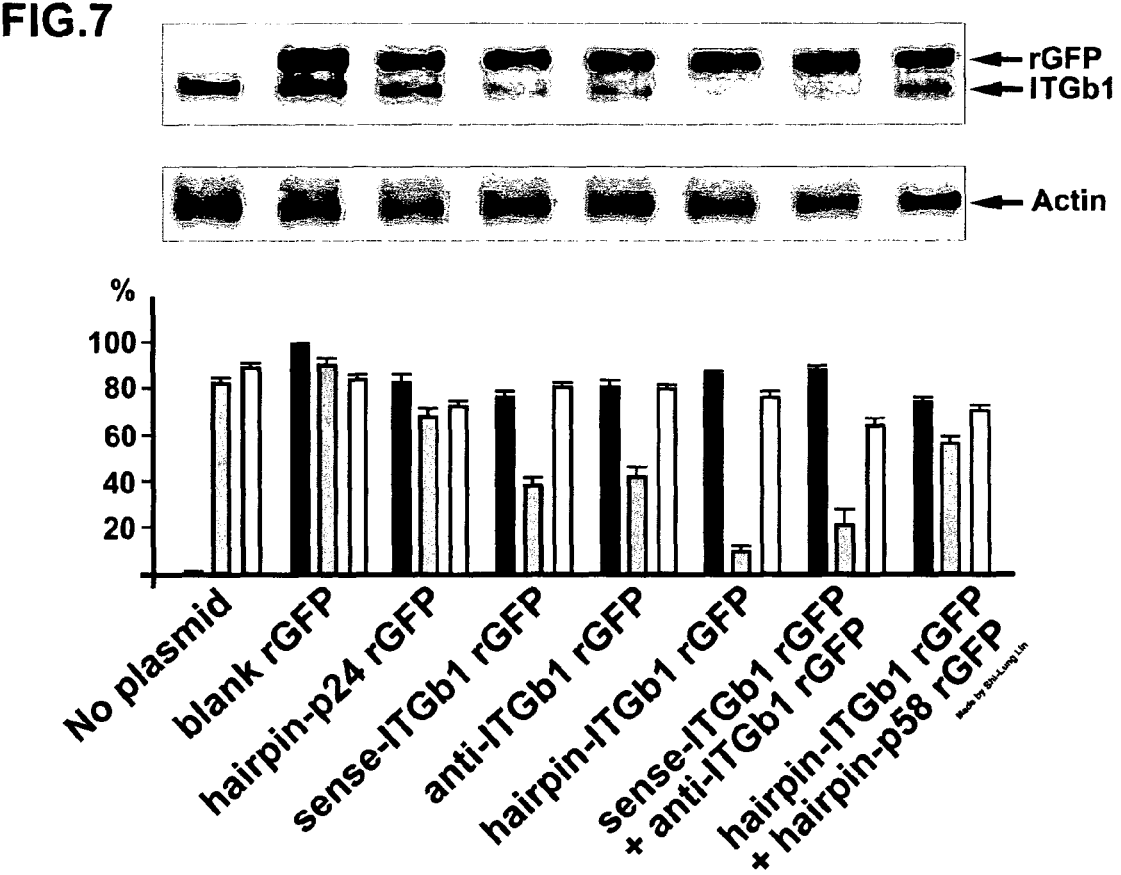
FIG. 7 depicts Western blot results, showing interference with integrin β1 (ITGb1) expression in human prostatic cancer LNCaP cells by various SpRNAi constructs.

11. Western Blot Analysis of RNA Splicing/processing-directed Integrin β1 Silencing As shown in FIG. 7, a similar splicing/processing-directed gene silencing phenomenon was seen in human cancerous LNCaP cells. Knockdown levels of integrin β1 (ITGb1) protein by various SpRNAi inserts were measured on a reduced 8% SDS-polyacrylamide gel. The relative amounts of rGFP (black bars), ITGb1 (gray bars) and actin (white bars) were shown on a percentage scale (Y axis). The ITGb1 levels (29 kDa) were significantly reduced by transfection of SpRNAi-rGFP genes containing a sense-ITGb1 (37.3%), antisense-ITGb1 (48.1%) and hairpin-ITGbl (13.5%) inserts, but not that of an intron-free rGFP gene (blank control) or SpRNAi-rGFP gene containing a hairpin-HIV p24 insert (negative control). Co-transfection of SpRNAi-rGFP genes containing sense- and antisense-ITGb1 inserts elicited a significant gene silencing effect (22.5%) and 10~15% cell death, while that of SpRNAi-rGFP genes containing hairpin-ITGb1 and hairpin-p58/HHR23 inserts partially blocked the splicing-directed gene silencing effect and resulted in an average of 57.8% expression level. These findings indicate that the SpRNAi-induced gene silencing effects may work on a wide range of genes and cell types of interest.

12. Combinational Therapy for HIV Eradication and Vaccination

The ex vivo transfection of a viral RNA-antisense DNA hybrid construct in conjunction with interleukin 2 adjuvant therapy was found to silence an average of 99.8% human immunodeficiency virus-1 (HIV-1) subtype B gene activity through a novel posttranscriptional gene silencing mechanism, deoxyribonucleotidylated RNA interference (D-RNAi; Lin et al. (2001) supra). This combined therapy not only delivered a strong suppression effect on viral replication but also boosted the immunity and proliferation of non-infected CD4+ T lymphocytes. A normal T cell outgrowth effect was observed to achieve maximal 76.2% HIV-infected cell elimination after one-week of therapy. RNA-directed endoribonuclease activity was mildly increased up to 6.7% by the transfection, while no interferon-induced cytotoxicity was detected. The cellular genes corresponding to combinational therapy have been further investigated by microarray analysis for AIDS prevention. Co-suppression of three microarray-identified target genes, Naf1β, Nb2 protein homologous to Wnt-6 and Tax1 binding protein was shown to prevent an average of 80.2% HIV-1b entry and infection in a primary CD4+ T cell model. These findings indicate an immediate therapy in both acute and chronic HIV-1 infections and also a potential vaccination useful for AIDS elimination.

In order to test the effectiveness of D-RNAi to inactivate HIV-1 replication, a viral RNA (vRNA)-antisense DNA (aDNA) hybrid construct was designed to silence an early-stage gene locus containing gag/pol/pro viral genes and p24 HIV-1 gene marker. The anti-gag/pol/pro transfection interferes with the integration of viral provirus into host chromosome and also prevents the activation of several viral genes, while the anti-p24 transfection provides a visual indicator for observing viral activity on an ELISA assay. The results showed that such strategy was effective in knocking out exogenous viral gene expression ex vivo in a CD4+ T lymphocyte extract model. Peripheral blood mononuclear cells (PBMC) extracted from patients were purified using CD4+-affinity immunomagnetic beads and grown in RPMI 1640 medium with 200 U/ml IL-2 adjuvant treatment for more than two weeks. A vRNA-aDNA hybrid probe containing partial HIV genomic sequence from +2113 to +2453 bases was generated using a pre-designed SpRNAi-recombinant gene (used as a control as described in previous sections) homologous to gag-p24 genes. After 96-h incubation, the expression activity of HIV-1 genome was measured by Northern blotting and found to be almost completely shut down in the D-RNAi hybrid transfection sets.

The gene silencing effects of anti-HIV D-RNAi transfections in the acute phase AIDS patient T lymphocyte extracts were biostatistically significant (n=3, p<0.01). Pure HIV-1 provirus was shown as a viral genome sized about 9.7 kb on a formaldehyde-containing RNA electrophoresis gel. Samples of CD4+ Th lymphocyte RNA extracts from normal, non-infected persons were used as negative controls, while those from HIV-1 infected patients were used as positive controls. No significant gene silencing effect was detected in all controls or transfections of other constructs, including vDNA-aRNA hybrid of HIV-1b, aDNA only and vRNA-aDNA against HTLV-1 rather than HIV-1. In the acute phase (<2-week infection), treatment with 5 nM D-RNAi knocked out an average of 99.8% viral gene expression, whereas in the chronic phase (~two-year infection), the same treatment knocked down only an average of 71.4% viral gene expression. Although higher RNase activities were found in chronic HIV-1+ T cells by microarray analysis, transfection of D-RNAi in higher concentration (more than 25 nM) can overcome this drug resistance. Unlike dsRNA, transfection of highly concentrated vRNA-aDNA hybrids did not cause significant interferon-induced cytotoxic effects, because the house-keeping gene, β-actin, was expressed normally in all sets of cells. Since the Northern blot method is able to detect HIV-1 gene transcript at the nanogram level, the above strong viral gene silencing effect suggests a very promising pharmaceutical and therapeutical potential for combinational administration of D-RNAi and IL-2 as antiviral therapy and/or vaccination.

Figure 8A:
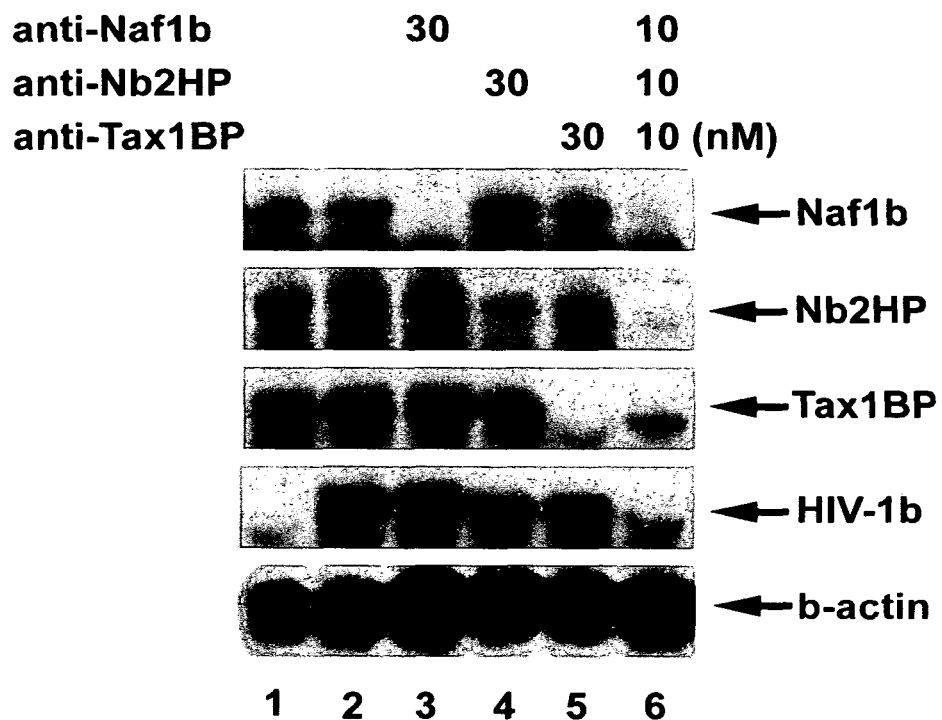
FIGS. 8A-B depict Northern blot analysis of SpRNAi-induced cellular gene silencing against HIV-1 infection (n=3).
Figure 8B:
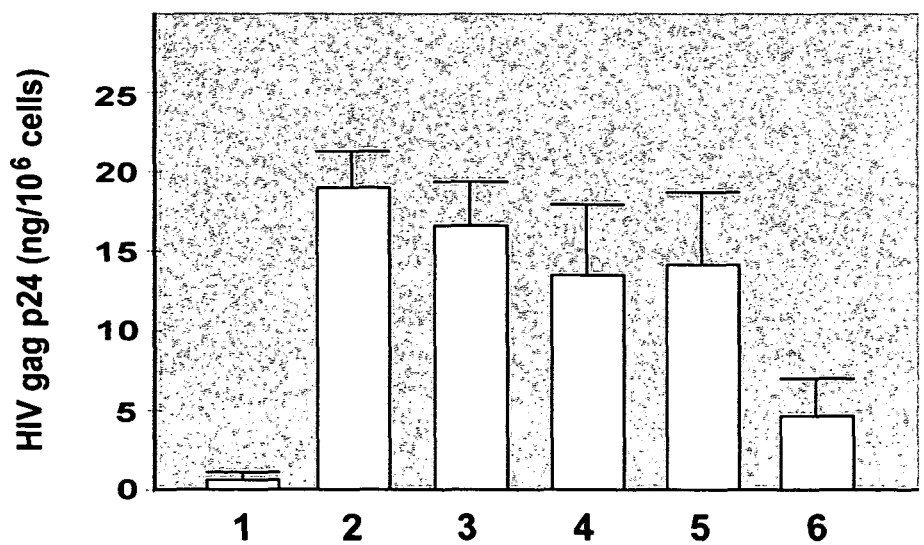
Figure 9:
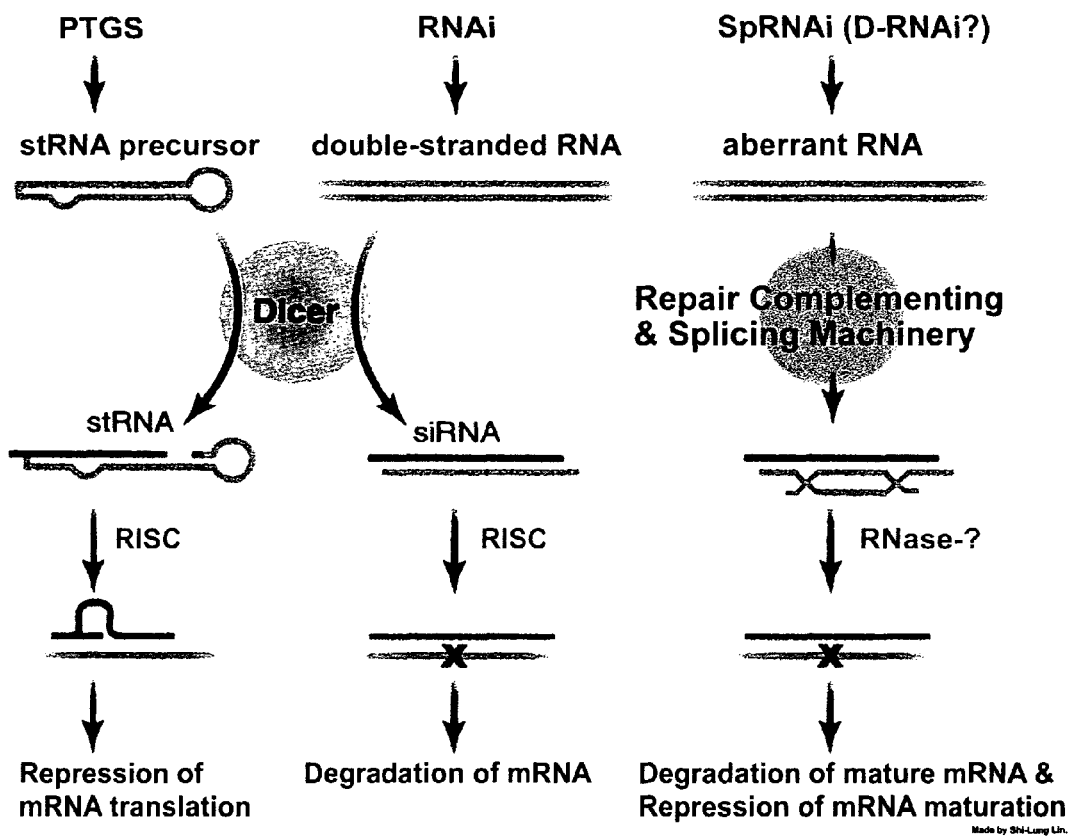
FIG. 9 depicts potential differences between traditional PTGS/RNAi and SpRNAi phenomena.

Northern blot analysis of SpRNAi-induced gene silencing effects on Naf1β, Nb2HP and Tax1BP was shown to prevent HIV-1 type B infection (FIG. 8). The tested gene targets were selected through RNA-PCR microarray analysis of differential expression genes from the acute (one~two weeks) and chronic (about two years) infected patients' primary T cells with or without 25 nM anti-HIV D-RNAi treatment (Lin et al. (2001) supra). The SpRNAi product concentrations in all treatments were normalized to 30 nM. FIG. 8B is a bar chart showing HIV-gag p24 ELISA results (white) in correlation with the treatment results demonstrated in FIG. 8A.

In view of CD4 function in IL-2 stimulation and T-cell growth and activation, CD4 may not be an ideal target for HIV prevention. However, the search for HIV-dependent cellular genes in vivo was hindered by the fact that infectivity of viruses and infection rate among different patients are usually different and lead to inconsistent results. Short-term ex vivo culture conditions can normalize infectivity and infection rate of HIV transmission in a more uniformed $CD4^+$ T cell population. Microarray analysis based on such ex vivo conditions would be reliable for critical biomedical and genetic research of HIV-1 infection. Microarray studies identified differential gene profiles between $HIV^-$ and $HIV^+$ T cells in the acute and chronic infection phases and provided many potential anti-HIV cellular gene targets for AIDS therapy and prevention. To functionally evaluate the usefulness of targeting cellular genes for HIV vaccination, three highly differentially expressed genes, Naf1β, Nb2 homologous protein to Wnt-6 (Nb2HP) and Tax1 binding protein (Tax1BP) were tested for inhibiting HIV-1 infection. Since each of these genes contributes to only a part of AIDS complications, knockdown of a single target gene failed to suppress HIV-1 infection, while combination of all three SpRNAi probes at the same total concentration showed a significant (80±10%) reduction in HIV-1b infection (FIG. 8A, n=3, p<0.01). The ELISA results of HIV gag-p24 protein (FIG. 8B) also correlated with the Northern blot data, showing an average of 77±5% reduction of gag-p24 expression. These findings indicate the feasibility of a novel strategy for retroviral vaccination using PTGS mechanisms against cellular target genes.

Two major phenomenal differences between PTGS/RNAi and SpRNAi mechanisms were found. First, the onset of SpRNAi effects takes a period of time more than 36-48 hours, which is longer than the timing needed for the onset of PTGS/RNAi (12-24 hours). Second, although the role of PTGS/RNAi-associated Dicer enzymes is unclear for the SpRNAi-directed gene silencing mechanism, several repair complementing antigens were found to be involved. Homologous recombination machinery involving nucleotide excision repair-related gene p58/HHR23 was found to play a potential role of Dicer in SpRNAi induction. The p58/HHR23 species that codes for XP-C repair-complementing proteins is a human homologue of yeast RAD23 derivatives, sharing an ubiquitin-like N-terminus. Based on its molecular similarity shared with RNA repairing-directed transcriptional regulation, the repair-complementing machinery indicates a novel mechanism of posttranscriptional gene silencing in addition to RNA interference.

Homologous recombination between intracellular mRNAs and the RNA components of a D-RNAi agent construct probably accounted for its specific gene silencing effect (Lin et al. (2001) *Current Cancer Drug Targets* 1: 241-247). $[p^{32}]$-labeled DNA component of a D-RNAi agent construct was found to be intact in a hybrid duplex during the effective period of a D-RNAi phenomenon, while the labeled RNA part was replaced by a cold homologue and degraded into small RNA oligoribonucleotides within a 3-day incubation period (FIG. 10A). It is possibly that the D-RNAi agent can facilitate the degradation of non-recombined parts of its mRNA homologue as shown in FIG. 10B. Alternatively, the newly recombined mRNA part of the D-RNAi agent may be further processed by intracellular Pol II and some unknown RNA excision machineries to generate miRNA-like molecules for long-term gene silencing. This is supported by the fact that both D-RNAi-derived small RNAs and Pol II RNA splicing-processed intron fragments have an average length of 15-45 nucleotides, which is comparable to the general sizes of Dicer-processed miRNA intermediates. Additionally, both kinds of small RNAs isolated by guanidinium-chloride ultracentrifugation can elicit strong, but short-term gene silencing effects to genes homologous to the small RNAs in cells, indicating the possible miRNA-related interfering property of these small RNAs. Since the small miRNA-like RNAs are constitutionally derived from the large templates of mRNA-cDNA or precursor mRNA-genomic DNA hybrids, the long-term effect of D-RNAi phenomena may be maintained by accumulation of sufficient small miRNA-like RNAs rather than the stability of small RNAs. This also explains the delayed initiation phase observed in the D-RNAi-induced gene silencing and intron splicing-mediated PTGS phenomena (Lin et al. (2001) *Biochem. Biophys. Res. Commun.* 281: 639-644; and Lin et al. (2003) *Biochem. Biophys. Res. Commun.*, in press).

Previous studies (Zhang et al. (1994) *Nature* 372: 809-812; and Ghosh and Garcia-Blanco (2000) *RNA* 6: 1325-1334) have demonstrated that a coupled interaction between nascent Pol II pre-mRNA transcription and intron excision occurs within certain nuclear region proximal to genomic DNA (i.e., perichromatin fibrils), indicating a reasonable potential for D-RNAi-associated miRNA generation in cells. The spliced introns are not completely digested into monoribonucleotides for transcriptional recycling, as approximately 10~30% of the introns are found in the cytoplasm with a moderate half-life (Nott et al. (2003) *RNA* 9: 607-617). In an effort to examine such a process, an artificial intron mimicking the natural structure of a pre-mRNA intron was constructed for evaluating splicing-directed small RNA generation (Lin et al. (2003) *Biochem. Biophys. Res. Commun.*, in press). The splicing-competent artificial intron, SpRNAi, is flanked by a splice donor (DS) and acceptor (AS) site, and contains a branch-point domain (BrP), a poly-pyrimidine tract (PPT) and at least one intronic insert located in the 5'-proximal domain of the artificial intron. To ensure the accuracy of pre-mRNA splicing, the SpRNAi also contains a translation stop codon in its 3'-proximal region, which if present in a cytoplasmic mRNA, would signal the diversion of the defective pre-mRNA from a non-sense mRNA degradation (NMD) pathway. As shown by results from low stringency Northern blotting, the intracellular processing of a spliced intron into small RNA fragments was found to be highly efficient. The release of small 15~45 nt RNA fragments was found to be only from the intron-containing gene transcripts, but not from an intronless mRNA or a splice-donor-defective pre-mRNA (a positive example of NMD). The small miRNA-like RNAs are able to trigger translation repression or sometimes RNA degradation depending on the degree of complementarity and homology with their targets. According to the variety and complexity of natural miRNA structures, there is no artificial means to produce intracellular miRNA-like molecules before the finding of this intron splicing-mediated gene silencing phenomenom. The process of such miRNA-like small interfering RNA generation is therefore different from that for the dsRNA-induced RNAi; however, the possible involvement of RNAi mechanisms cannot be ruled out in that some small RNAs might form siRNAs by complementary hybridization within a localized compartment.

13. In Vivo Gene Silencing Using D-RNAi Agents

Figure 11:
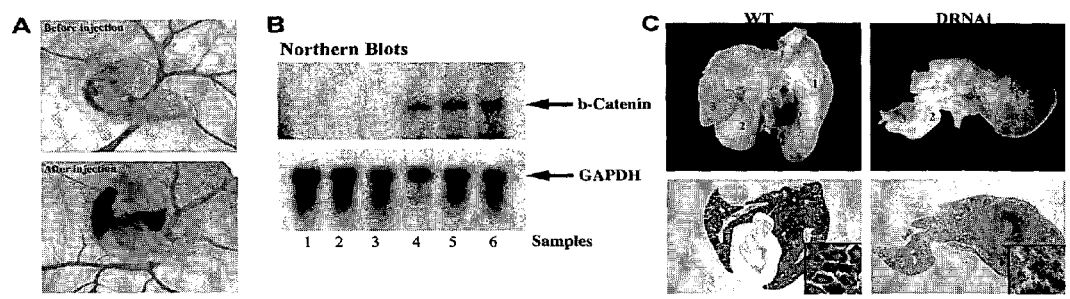
FIGS. 11A-C depict in vivo gene silencing by anti-β-catenin D-RNAi in embryonic chicken.

D-RNAi can be used as an effective strategy to silence specific target gene in vivo. β-catenin gene was selected as an example because its product plays a critical role in the biological development and ontogenesis. β-catenin is known to be involved in the growth control of skin and liver tissues in chicken embryos. As shown in FIG. 11, experimental results demonstrated that D-RNAi (mRNA-cDNA hybrid) agents were capable of inhibiting β-catenin gene expression in the liver and skin of developing chicken embryos. The anti-β-catenin D-RNAi molecules were generated against the central region (aa 306-644) of the β-catenin coding sequence (Gen-Bank Access No. X87838) by RNA-PCR. Fertilized eggs were obtained from SPAFAS farm (Preston, Conn.) and incubated in a humidified incubator. Using embryonic day 3 chicken embryos, a dose of 25 nM of the D-RNAi agent or reversal control hybrids of sense DNA-antisense RNA (sDNA-aRNA) was injected into the ventral body cavity, which is close to where the liver primordia would form (FIG. 11A). The mRNA-cDNA or the control sDNA-aRNA hybrids were mixed with DOTAP® liposomal transfection reagent (Roche) at a ratio of 3:2. A 10% (v/v) fast green solution was added before injection as a dye indicator. The mixtures were injected into the ventral side near the liver primordia and below the heart using heat pulled capillary needles. After injection, the eggs were sealed with scotch tape and put back into the humidified incubator at 39-40° C. until day 12 when the embryos were removed, examined and photographed under a dissection microscope. While there were malformations, the embryos survived and there was no visible overt toxicity or overall perturbation of embryo development. The liver was the closest organ to the injection site and was most dramatically affected in its phenotypes. Other regions, particularly the skin, were also affected by the diffused D-RNAi agent. As shown in FIG. 11B, Northern blot hybridizations using RNA from dissected livers showed that β-catenin in the control livers remained expressed (lanes 4-6), whereas the level of β-catenin mRNA was decreased dramatically (lanes 1-3) after treatment with the D-RNAi agent directed against β-catenin. Controls used included liposome alone (lane 4) and of control sDNA-aRNA hybrids in similar concentrations (lanes 5 and 6).

Figure 12:
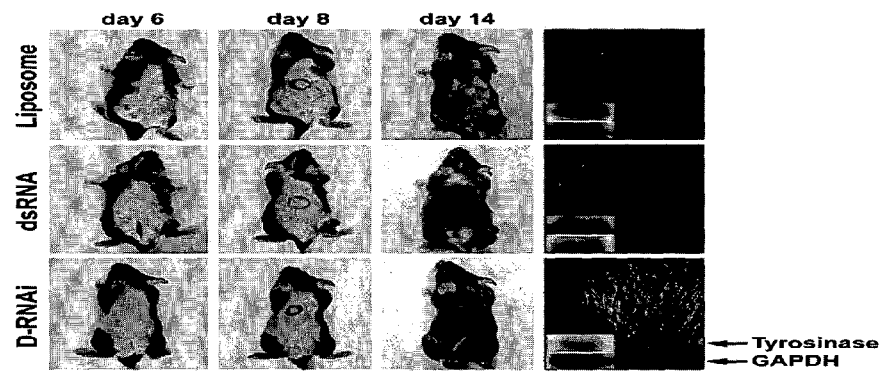
FIG. 12 depicts in vivo gene silencing by anti-tyr D-RNAi in mouse.

After ten days of injection with the anti-β-catenin D-RNAi (mRNA-cDNA hybrid) agent, the embryonic chicken livers showed an enlarged and engorged first lobe, but the size of the second and third lobes of the livers were dramatically decreased (FIG. 11C). Histological sections of normal livers showed hepatic cords and sinusoidal space with few blood cells. In anti-β-catenin D-RNAi-treated embryos, the general architecture of the hepatic cells in lobes 2 and 3 remained unchanged; however, there were islands of abnormal regions in lobe 1. The endothelium development appeared to be defective and blood leaked outside of the blood vessels. Abnormal types of hematopoietic cells were also observed between hepatocytes, particularly dominated by a population of small cells with round nuclei and scanty cytoplasm. In severely affected regions, hepatocytes were disrupted (FIG. 11C, small windows). These results showed that the anti-β-catenin D-RNAi agent was very effective in knocking out the targeted gene expression at a very low dose of 25 nM and was effective over a long period of time (>10 days). Furthermore, the anti-β-catenin D-RNAi gene silencing effect appeared to be very specific, as non-targeted organs appeared to be normal, indicating that the D-RNAi hybrid compositions had no overt toxicity. The gene silencing in chicken and mice by the D-RNAi agent (FIGS. 11 and 12) presents a great potential of localized transgene-like approach in creating animal models for human diseases.

To test in an adult animal model (FIG. 12), patched albino (white) skins of melanin-knockout mice (Rosa-26 strain) were created by a succession of intra-cutaneous (i.c.) transduction of about 50 nM anti-tyrosinase (tyr) mRNA-cDNA hybrids for 4 days (a total of 200 nM). Tyr, a type-I membrane protein and copper-containing enzyme, catalyzes the critical and rate-limiting step of tyrosine hydroxylation in the biosynthesis of melanin (black pigment) in skins and hairs. After 14-day incubation, the expression of melanin was blocked due to the loss of its intermediates resulted from the tyr silencing effect. In contrast, the blank control and dsRNA-transfected mice showed normal skin color (black), indicating that the loss of melanin is specifically caused by the mRNA-cDNA transfection. Moreover, Northern blot analysis using RNA-PCR-derived mRNAs from hair follicles showed a 76.1±5.3% reduction in tyr expression 2 days after the transfection of the D-RNAi agent, which was consistent with the immunohistochemistry results from the same skin area, whereas mild, non-specific degradation of common gene transcripts was detected in the dsRNA-transfected skins, shown by the smearing patterns of both the house-keeping control GAPDH and tyr mRNAs in Northern blots ($4^{th}$ column, left-bottom insert windows). These results show that the utilization of D-RNAi agents provides a powerful new strategy for in vivo gene therapy, potentially to melanoma. At the same dosage (200 nM in total), the D-RNAi transfections did not cause detectable cytotoxicity, while the dsRNA transfections induced noted non-specific mRNA degradation. This even underscores the fact that the mRNA-cDNA hybrids are effective even under in vivo systems without the side-effects of dsRNA. The results also indicate that this gene silencing effect is stable and efficient in knocking out target gene expression over a relatively long period of time since the hair regrowth requires at least a ten-day recovery. Further, it was observed that non-targeted skin hairs appeared to be normal, indicating that the compositions used herein possess high specificity and no overt toxicity. Thus, the D-RNAi-based gene manipulation offers the advantages of low in vivo dosage, stability, long-term effectiveness, and lack of overt toxicity.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. An isolated RNA comprising:
an artificial intron comprising a splice donor site, a splice acceptor site, a branch site, a poly-pyrimidine tract and at least one aberrant RNA selected from the group consisting of a short-temporary RNA, small-interfering RNA, short-hairpin RNA, long deoxyribonucleotide-containing RNA and ribozyme RNA,
wherein said aberrant RNA is an RNA capable of silencing a target gene when released in a cell.

2. The isolated RNA of claim 1, wherein the cell is a mammalian cell.

3. The isolated RNA of claim 1, wherein the splice donor site contains 5'-AGGUAAGU-3'.

4. The isolated RNA of claim 1, wherein the splice acceptor site contains 5'-CCACAGC-3'.

5. The isolated RNA of claim 1, wherein the branch site contains 5'-UACUAAC-3.

6. The isolated RNA of claim 1, wherein the cell is a eukaryotic cell.

7. An isolated RNA comprising:
an artificial intron RNA comprising at least one aberrant RNA selected from the group consisting of a short-temporary RNA, small-interfering RNA, short-hairpin RNA, long deoxyribonucleotide-containing RNA (D-RNA) and ribozyme RNA, said aberrant RNA being capable of silencing a target gene when released in a eukaryotic cell and wherein the artificial intron RNA further comprises a splice donor site that includes 5'-AGGUAAGU-3', a splice acceptor site that includes 5'-CCACAGC-3', a branch site that includes 5'-UACUAAC-3', a poly-pyrimidine tract that includes 5'-UUCUUUUUUC-3' (SEQ ID NO:2), or a combination thereof.

8. A cultivated cell comprising the isolated RNA of claim 1.

9. A composition comprising the isolated RNA of claim 1.

10. The isolated RNA of claim 1, wherein the artificial intron contains a sequence that targets an exon of the target gene, wherein the target gene is integrin β1.

11. The isolated RNA of claim 6, wherein the artificial intron contains a sequence that targets an exon of the target gene, wherein the target gene is integrin β1.

12. The isolated RNA of claim 7, wherein the artificial intron contains a sequence that targets an exon of the target gene, wherein the target gene is integrin β1.

\* \* \* \* \*